United States Patent
Mieno

(10) Patent No.: US 10,458,898 B2
(45) Date of Patent: Oct. 29, 2019

(54) METHOD FOR PREDICTING FRICTIONAL RESISTANCE OF ROUGH SURFACE, AND APPARATUS FOR ESTIMATING SURFACE PERFORMANCE

(71) Applicant: CHUGOKU MARINE PAINTS, LTD., Otake-shi (JP)

(72) Inventor: Hirohisa Mieno, Otake (JP)

(73) Assignee: CHUGOKU MARINE PAINTS, LTD., Otake-shi (JP)

( * ) Notice: Subject to any disclaimer, the term of this patent is extended or adjusted under 35 U.S.C. 154(b) by 106 days.

(21) Appl. No.: 15/548,539

(22) PCT Filed: Jan. 29, 2016

(86) PCT No.: PCT/JP2016/052612
§ 371 (c)(1),
(2) Date: Aug. 3, 2017

(87) PCT Pub. No.: WO2016/125695
PCT Pub. Date: Aug. 11, 2016

(65) Prior Publication Data
US 2018/0017482 A1    Jan. 18, 2018

(30) Foreign Application Priority Data
Feb. 5, 2015    (JP) ................. 2015-021306

(51) Int. Cl.
*G01N 19/00*    (2006.01)
*G01B 11/30*    (2006.01)
(Continued)

(52) U.S. Cl.
CPC ......... *G01N 19/02* (2013.01); *G01B 11/0608* (2013.01); *G01B 11/303* (2013.01); *G01D 5/347* (2013.01); *G01N 2013/0216* (2013.01)

(58) Field of Classification Search
None
See application file for complete search history.

(56) References Cited

U.S. PATENT DOCUMENTS 6,324,480 B1    11/2001  Takahashi et al.
2010/0220337 A1*  9/2010  Lee ................... G01B 11/0608
                                                  356/516
2015/0081231 A1    3/2015  Mieno

FOREIGN PATENT DOCUMENTS

JP    11-342889 A      12/1999
WO    2013/153877 A1   10/2013

OTHER PUBLICATIONS

Schultz, "The Relationship Between Frictional Resistance and Roughness for Surfaces Smoothed by Sanding" Journal of Fluids Engineering, vol. 124, 2002 (Year: 2002).*

(Continued)

*Primary Examiner* — John C Kuan
(74) *Attorney, Agent, or Firm* — Oblon, McClelland, Maier & Neustadt, L.L.P.

(57) ABSTRACT

The invention provides a method which predicts a ratio of the increase in frictional resistance of a rough surface in a simple manner, quickly and without variations in predicted results among individuals. The method for predicting the frictional resistance of a rough surface having a variation in roughness wavelength, and being in contact with a fluid flowing at varied velocities includes evaluating the total projected area of all prominent peaks standing out above the viscous sublayer thickness per unit area, and calculating the friction increase ratio FIR (%) or the frictional resistance increase Δτ.

16 Claims, 8 Drawing Sheets

(51) Int. Cl.
G01B 11/06 (2006.01)
G01N 13/02 (2006.01)
G01D 5/347 (2006.01)
G01N 19/02 (2006.01)

(56) References Cited

OTHER PUBLICATIONS

Demirel et al., "A CFD model for the frictional resistance prediction of antifouling coatings" Ocean Engineering 89 (2014) 21-31 (Year: 2014).*
Extended European Search Report dated Jun. 14, 2018 in Patent Application No. 16746526.9.
Keizo Tokunaga, et al., "Approximate Calculation of Ship Frictional Resistance Increase due to Surface Roughness", Journal of the Society of Naval Architects of Japan, vol. 1982, No. 152, XP055481867, Jan. 1982, pp. 55-61.
H. Mieno, et al., "Friction Increase due to Roughness of Ship Hull Paint," Journal of the Japan Institute of Marine Engineering, May 2013, vol. 48, No. 3, with English abstract and translation, 21 pages.
"Fluid Mechanics, JSME Text Series," 2007, The Japan Society of Mechanical Engineers, 3 pages.
International Search Report dated Apr. 26, 2016 in PCT/JP2016/052612 filed Jan. 29, 2016.

* cited by examiner

[FIG. 1]
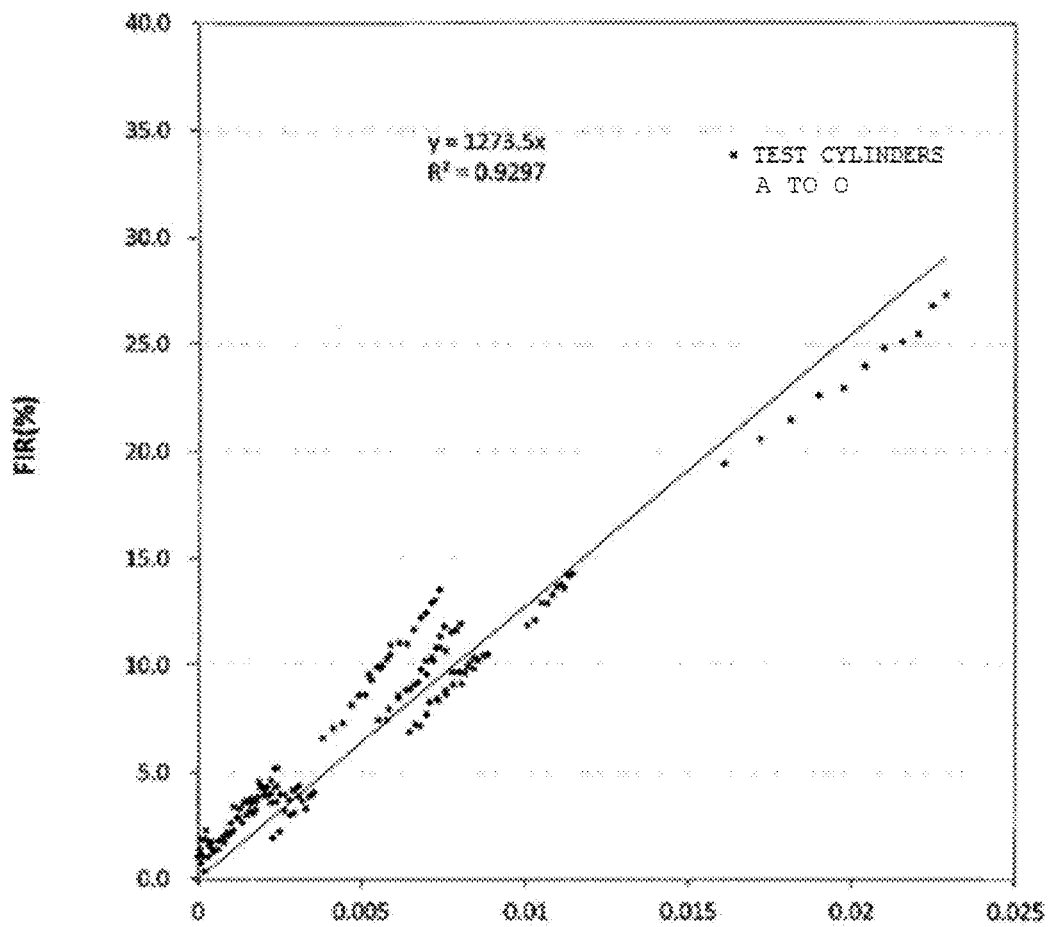
RELATIONSHIP BETWEEN FRICTION INCREASE RATIO FIR (%) AND
PROMINENT PEAK PROJECTED AREA $A = 0.5 \times (Rc - \delta s)^2/(Rc \times RSm)$

[FIG. 2]
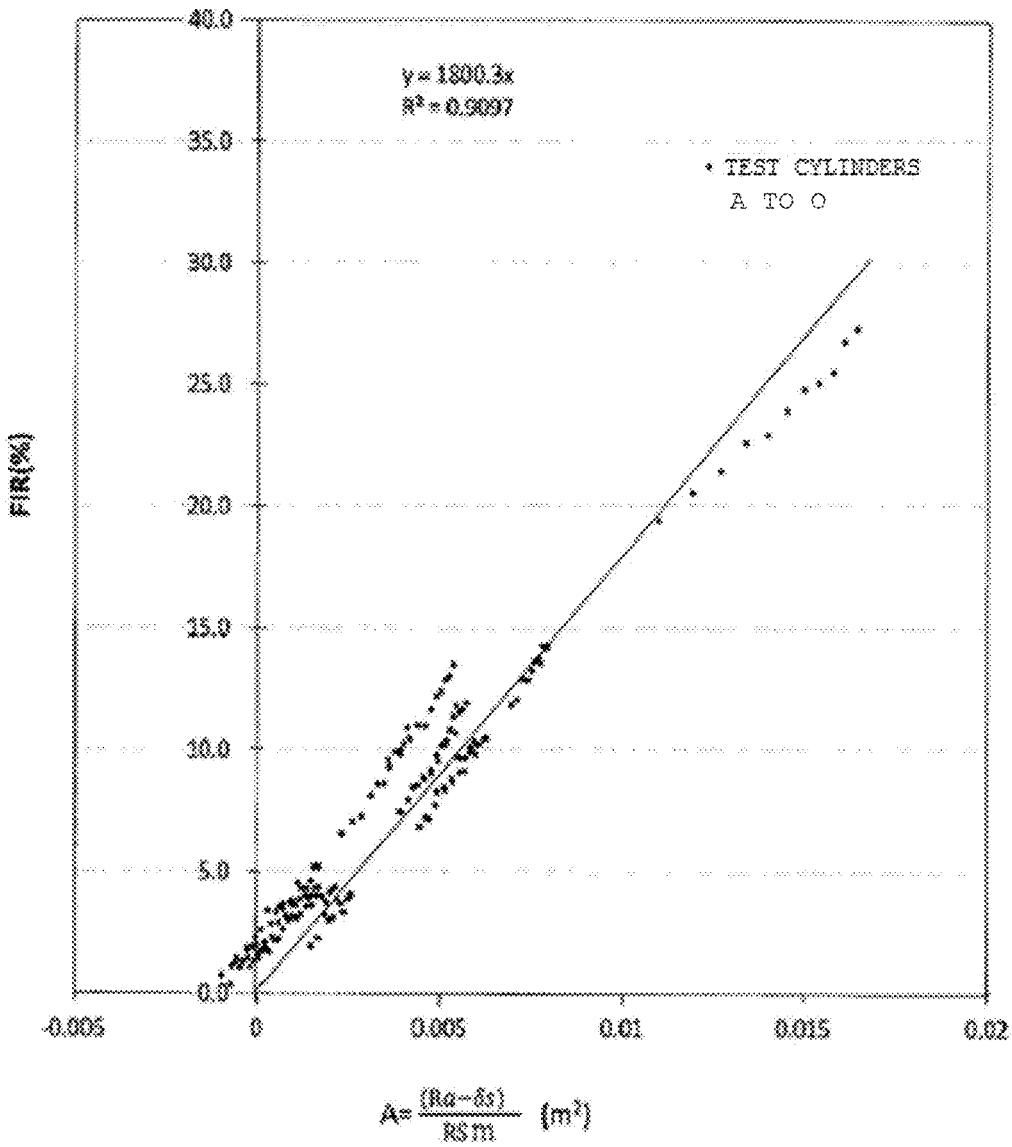
RELATIONSHIP BETWEEN FRICTION INCREASE RATIO FIR (%) AND
PROMINENT PEAK PROJECTED AREA $A = (Ra - \delta z)/RSm$

[FIG. 3]
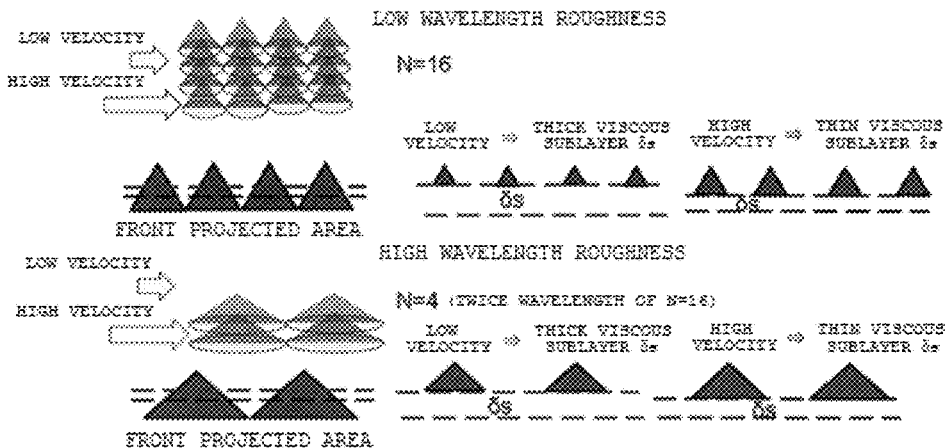
A schematic view illustrates a change of δs and prominent peak projected area by a change in flow velocity.
[FIG. 4]
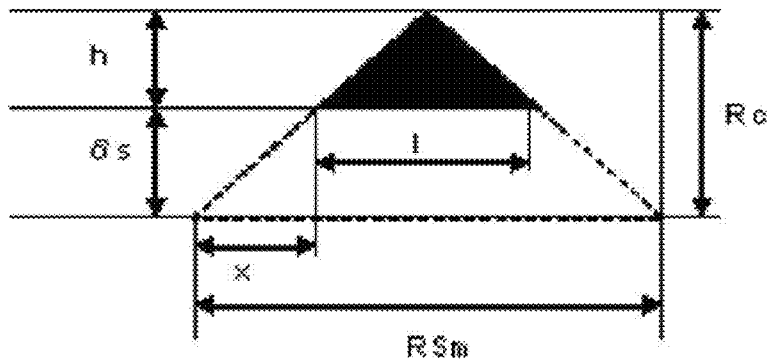
CALCULATION OF PROMINENT PEAK PROJECTED AREA A FROM VISCOUS SUBLAYER δs USING Rc

[FIG. 5]
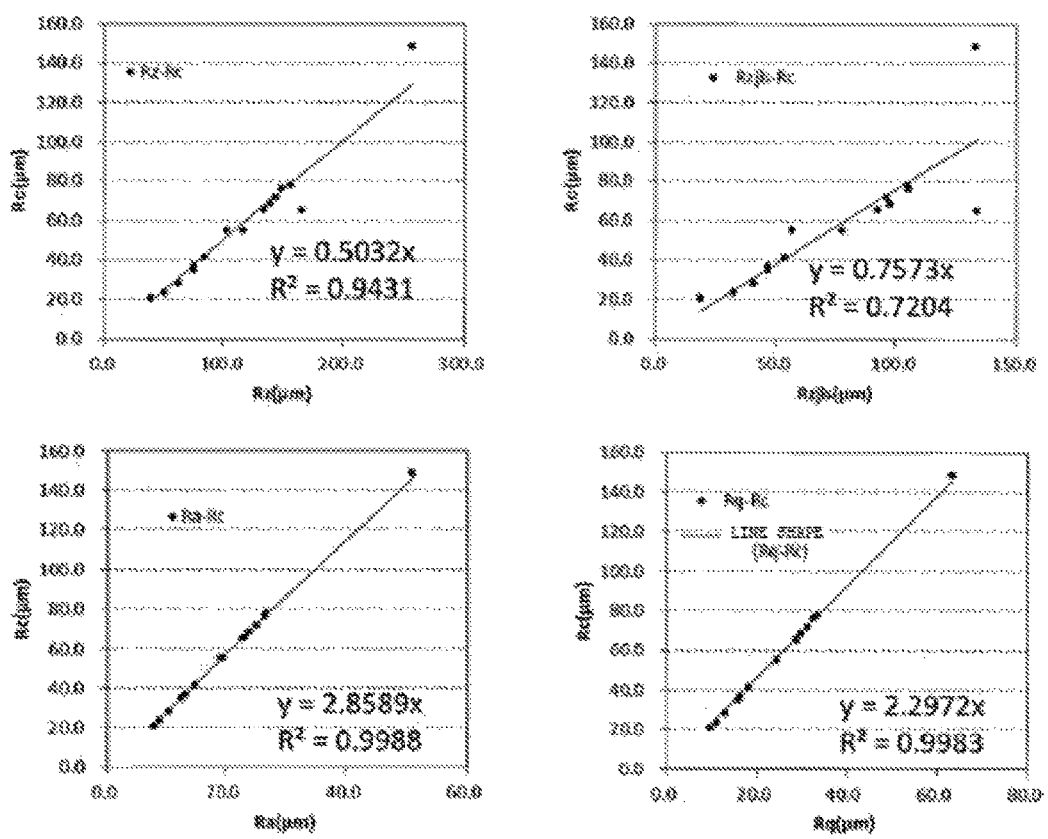
CORRELATIONS OF Rc WITH PARAMETERS

[FIG. 6]
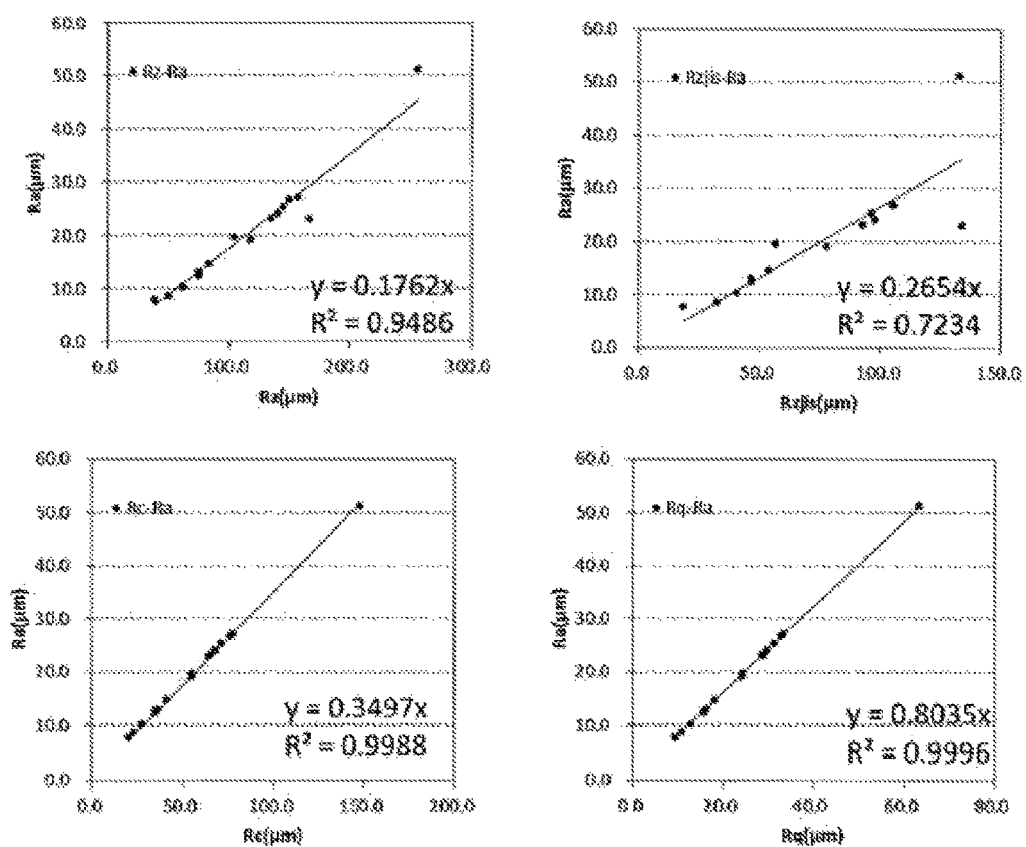
CORRELATIONS OF Ra WITH PARAMETERS

[FIG. 7]
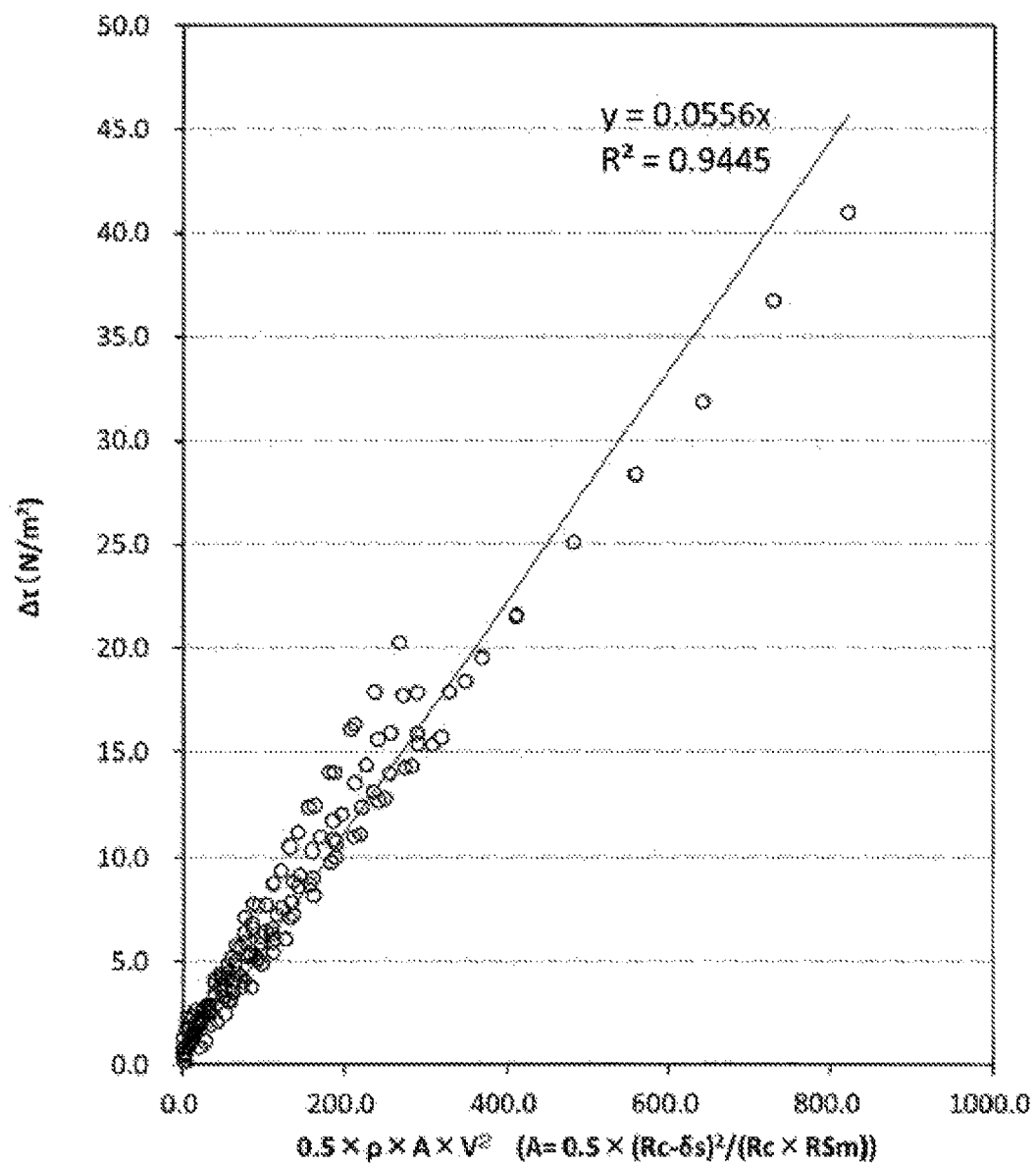
RELATIONSHIP BETWEEN $\Delta\tau$ (N/m²) AND $0.5 \times \rho \times A \times V^2$
$A = 0.5 \times (Rc - \delta s)^2 / (Rc \times RSm)$

[FIG. 8]
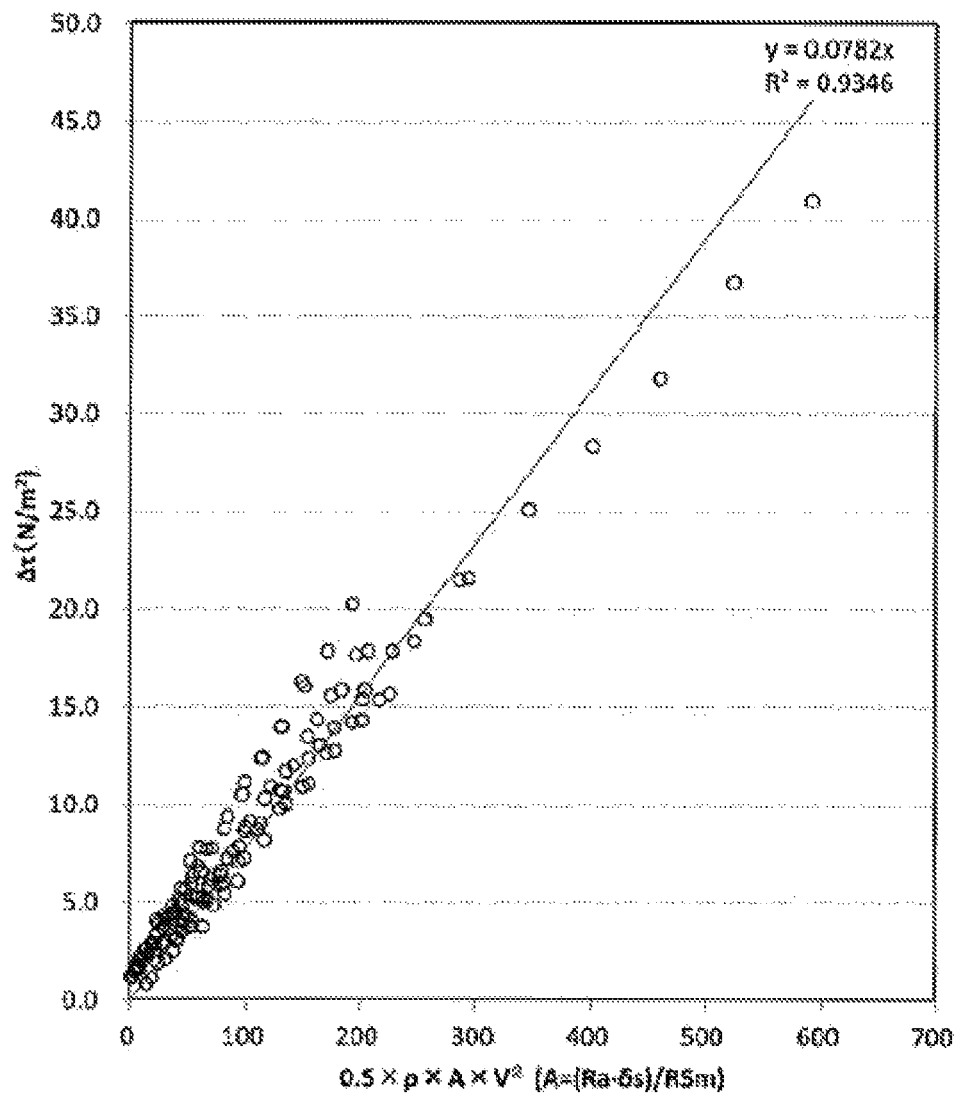
RELATIONSHIP BETWEEN $\Delta\tau$ (N/m$^2$) AND $0.5 \times \rho \times A \times V^2$
$A = (Ra - \delta s)/RSm$

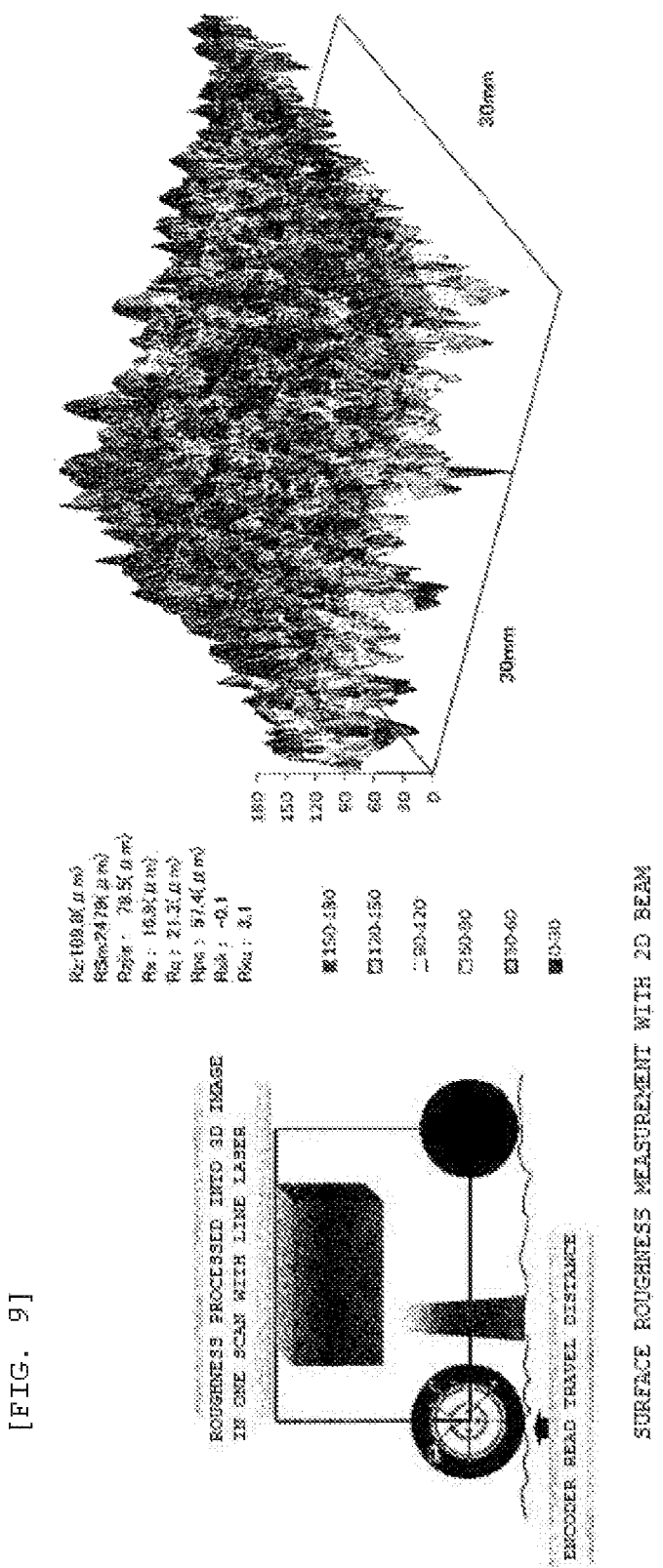
[FIG. 9]

METHOD FOR PREDICTING FRICTIONAL RESISTANCE OF ROUGH SURFACE, AND APPARATUS FOR ESTIMATING SURFACE PERFORMANCE

TECHNICAL FIELD

The present invention relates to a method which predicts an increase in frictional resistance of a rough surface in contact with a fluid in a simple manner, quickly and without variations in predicted results among individuals, and to an apparatus which estimates an increase in frictional resistance using the prediction method.

BACKGROUND ART

Increase in frictional resistance due to roughness on a surface is an important issue in, for example, improving the performance of ships or designing piping and flow channels. The surface roughness of a rough surface is considered as the main cause of an increase in frictional resistance. Since old times, efforts have been made to predict an increase in frictional resistance based on surface roughness. General methods which estimate an impact of surface roughness of an inside surface of a pipe involve Moody diagrams or Colebrook equation as described in Non Patent Document 1. Although such methods can be applied to fluids having various flow velocities or various viscosities, the range of roughness wavelengths which can be studied is limited because of the fact that the surface that is evaluated is rendered rough by the attachment of sand grains and therefore the roughness wavelengths are dependent on the grain size of the sand grains. Further, these methods using Moody diagrams or Colebrook equation only take into consideration a relationship between the pipe diameter and the relative roughness height, and neglect profile parameters such as roughness wavelength. On the other hand, methods described in Patent Document 1 and Non Patent Document 2 are used to study the roughness on hulls. The methods of these documents focus on the roughness wavelength and calculate the ratio of the increase in frictional resistance based on a relationship of the square of roughness height and the roughness wavelength. However, the relationship that is studied in these documents assumes that the flow velocity is constant, with no attentions being paid to friction at various flow velocities. In practice, the resistance offered by roughness is increased to various degrees depending on the flow velocity (the speed of a ship or the flow rate in a pipe). Thus, the increase in resistance needs to be calculated at each of the expected flow velocities. However, none has disclosed a method which can predict how much a rough surface with various roughness wavelengths will increase the frictional resistance when in contact with a fluid at various flow velocities, with high accuracy based on surface roughness.

CITATION LIST

Patent Document

Patent Document 1: WO 2013 153877

Non Patent Document

Non Patent Document 1: The Japan Society of Mechanical Engineers, "Fluid Mechanics, JSME Text Series", (2007), p. 99

Non Patent Document 2: Hirohisa Mieno, Hiroshi Masuda, "Friction Increase due to Roughness of Ship Hull Paint", Journal of THE JAPAN INSTITUTE OF MARINE ENGINEERING, Vol. 48, No. 3 (2013), pp. 300-307

SUMMARY OF INVENTION

Technical Problem

The invention presents a method which predicts the frictional resistance of a rough surface at various flow velocities of a fluid, and an apparatus which estimates surface performance using the method.

Solution to Problem

Under the circumstances discussed above, the present inventors carried out extensive studies on methods and apparatuses which can predict an increase in frictional resistance of a rough surface having various wavelengths at various flow velocities of a fluid. As a result, the present inventors have found that the configurations described below make it possible to predict an increase in frictional resistance offered by a rough surface having various wavelengths, thus completing the present invention.

[1]
A method for predicting the frictional resistance of a rough surface having a variation in roughness wavelength, and being in contact with a fluid flowing at varied velocities, the method including evaluating the total projected area A of all prominent peaks standing out above the viscous sublayer thickness per unit area (hereinafter, written as the "prominent peak projected area A"), and calculating the friction increase ratio FIR (%) using Equation (1) below or the frictional resistance increase $\Delta\tau$ using Equation (2) below.

[Math. 1]
$$FIR\ (\%) = C \times A \tag{1}$$

[Math. 2]
$$\Delta\tau = C_r \frac{1}{2} \rho A V^2 \tag{2}$$

(In Equation (1), the coefficient C is a constant dependent on the prominent peak projected area A and is determined by performing a frictional resistance test beforehand in which the frictional resistance is measured with respect to a plurality of rough surfaces differing in the degree of roughness while changing the flow velocity V and the friction increase ratios FIR (%) of the rough surfaces are calculated wherein the friction increase ratios FIR (%) are percentages of the difference $\tau_r - \tau_0$ between the frictional resistance $\tau_r$ of the rough surface and the frictional resistance $\tau_0$ of a smooth surface, divided by $\tau_0$.

In Equation (2), the coefficient $C_r$ is a constant dependent on the fluid density $\rho$, the prominent peak projected area A and the flow velocity V and is determined from the relation of Equation (2) using values of frictional resistance increase $\Delta\tau$ obtained beforehand by a frictional resistance test in which the frictional resistance is measured with respect to a plurality of rough surfaces differing in the degree of roughness while changing the flow velocity V wherein the values of frictional resistance increase $\Delta\tau$ are the differences $\tau_r - \tau_0$ between the frictional resistance $\tau_r$ of the rough surface and the frictional resistance $\tau_0$ of a smooth surface.)

[2]

The method for predicting the frictional resistance of a rough surface described in [1], wherein the prominent peak projected area A is a value calculated using Equation (3) wherein RSm is the average length of roughness curve elements and Rc is the average height of roughness curve elements both measured as roughness wavelength λ and roughness height R, respectively, in accordance with the regulations in ISO 4287: 1997 (JIS B 0601: 2001).

[Math. 3]

$$A = 0.5 \times \frac{(Rc - \delta s)^2}{Rc \times RSm} \quad (3)$$

(In Equation (3), δs is the viscous sublayer thickness measured by a frictional resistance test with respect to a smooth surface and is a value determined in such a manner that the frictional velocity u* is calculated from the frictional resistance $\tau_0$ of the smooth surface using Equation (5), δs is calculated from Equation (4) using the dimensionless distance $y^+$ ($2<y^+<8$) and the kinematic viscosity coefficient ν of a fluid of interest, and, from among the values of δs thus calculated, the value which provides a high coefficient of correlation between FIR (%) or Δτ and the prominent peak projected area A in Equation (1) or (2) is selected).

[Math. 4]

$$\delta s = \frac{y^+ \times v}{u^*} \quad (4)$$

[Math. 5]

$$u^* = \sqrt{\frac{\tau_0}{\rho}} \quad (5)$$

[3]

The method for predicting the frictional resistance of a rough surface described in [2], wherein the prominent peak projected area A is calculated in such a manner that Rz, Rzjis, Rq or Ra is measured as roughness height R', the slope a of the Rc to the measured parameter is determined and the parameter is converted assuming that Rc=a×R' (R' is Rz, Rzjis, Rq or Ra).

[4]

The method for predicting the frictional resistance of a rough surface described in [1], wherein the prominent peak projected area A is a value calculated using Equation (6) wherein RSm is the average length of roughness curve elements and Ra is the arithmetic average roughness both measured as roughness wavelength λ and roughness height R, respectively, in accordance with the regulations in ISO 4287: 1997 (JIS B 0601: 2001).

[Math. 6]

$$A = \frac{(Ra - \delta s)}{RSm} \quad (6)$$

(In Equation (6), δs used to calculate the prominent peak projected area A is the viscous sublayer thickness measured by a frictional resistance test with respect to a smooth surface and is a value determined in such a manner that the frictional velocity u* is calculated from the frictional resistance $\tau_0$ of the smooth surface using Equation (5), δs is calculated from Equation (4) using the dimensionless distance $y^+$ ($2<y^+<8$) and the kinematic viscosity coefficient ν of a fluid of interest, and, from among the values of δs thus calculated, the value which provides a high coefficient of correlation between FIR (%) or Δτ and the prominent peak projected area A in Equation (1) or (2) is selected).

[5]

The method for predicting the frictional resistance of a rough surface described in [4], wherein the prominent peak projected area A is calculated in such a manner that Rz, Rzjis, Rq or Rc is measured as roughness height R", the slope a of the Ra to the measured parameter is determined and the parameter is converted assuming that Ra=a×R" (R" is Rz, Rzjis, Rq or Rc).

[6]

A surface performance estimating apparatus for estimating surface performance by the prediction method described in any of [1] to [5], the apparatus including:

a measurement section configured to measure the roughness height R and the average length RSm of roughness curve elements, and a calculation unit configured to calculate the prominent peak projected area A and to calculate the friction increase ratio FIR (%) using Equation (1) or the frictional resistance increase Δτ using Equation (2).

[7]

The surface performance estimating apparatus described in [6], wherein the measurement section is configured to measure the roughness height R and the average length RSm of roughness curve elements of three dimensional roughness while reading the travel distance with a rotary encoder or a linear encoder and reading the displacement with a laser displacement meter using a two-dimensional beam.

[8]

The surface performance estimating apparatus described in [6] or [7], wherein the roughness height R measured is Rz, Rzjis, Rq, Rc or Ra.

Advantageous Effects of Invention

The method according to the present invention can calculate an increase in frictional resistance due to roughness at various flow velocities of a fluid, directly by a very simple evaluation of roughness. The use of this method makes it possible to determine the grade of treatment or the type of treatment performed or to be performed on the surface that will be brought into contact with a fluid flowing at a flow velocity of interest.

BRIEF DESCRIPTION OF DRAWINGS

FIG. 1 is a diagram illustrating a relationship between the friction increase ratio FIR (%) and the prominent peak projected area A=0.5×(Rc−δs)$^2$/(Rc×RSm).

FIG. 2 is a diagram illustrating a relationship between the friction increase ratio FIR (%) and the prominent peak projected area A=(Ra−δs)/RSm.

FIG. 3 is a schematic view illustrating a change of δs and prominent peak projected area by a change in flow velocity.

FIG. 4 is a schematic view illustrating how the projected area a of a peak standing out above the viscous sublayer thickness δs is calculated using Rc.

FIG. 5 is a set of diagrams illustrating relationships of Rc and roughness parameters Rz, Ra, Rq and Rzjis.

FIG. 6 is a set of diagrams illustrating relationships of Ra and roughness parameters Rz, Rc, Rq and Rzjis.

FIG. 7 is a diagram illustrating a relationship between Δτ (N/m$^2$) and $0.5 \times \rho \times A \times V^2$ wherein $A=0.5 \times (Rc-\delta s)^2/(Rc \times RSm)$.

FIG. 8 is a diagram illustrating a relationship between Δτ (N/m$^2$) and $0.5 \times \rho \times A \times V^2$ wherein $A=(Ra-\delta s)/RSm$.

FIG. 9 is a schematic view of surface roughness measurement using a two-dimensional beam.

DESCRIPTION OF EMBODIMENTS

The present invention will be described in detail hereinbelow.

An aspect of the invention resides in a method for predicting an increase in frictional resistance due to a rough surface by evaluating the total projected area A of all prominent peaks standing out above the viscous sublayer thickness per unit area, and calculating the friction increase ratio FIR (%) or the frictional resistance increase Δτ.

Concepts of the Present Invention

FIG. 3 illustrates rough surfaces having different roughness wavelengths. As illustrated, a variation in flow velocity brings about a change in δs, which is the thickness of a layer free from influences of roughness, causing a change in prominent peak projected area. At a higher flow velocity, the viscous sublayer becomes smaller and the prominent peak projected area A is increased; thus, the friction increase ratio FIR (%) will be higher. Provided that the flow velocity is the same, the prominent peak projected area A is larger as the roughness is larger; the prominent peak projected area A is larger as the number of peaks is increased, i.e., as the roughness wavelength is shorter. In this case too, the friction increase ratio FIR (%) will be increased. The present inventors believed that an increase in frictional resistance due to roughness on a surface could be easily predicted if it was possible to reveal how the roughness height, the wavelength and the viscous sublayer thickness played roles in bringing about an increase in resistance, thus completing the present invention.

Calculation of Total Prominent Peak Projected Area A Per Unit Area from Roughness Parameters Any of Rc (the average height of roughness curve elements) and Ra (the arithmetic average roughness) is measured as the roughness height R in accordance with the regulations in JIS B 0601: 2001 (ISO 4287: 1997), and the total projected area A of all prominent peaks standing out above the viscous sublayer per unit area ((hereinafter, written as the "prominent peak projected area A")) is calculated using Equation (1) or (2) below.

[Math. 7]

$$A = 0.5 \times \frac{(Rc - \delta s)^2}{Rc \times RSm} \quad (1)$$

[Math. 8]

$$A = \frac{(Ra - \delta s)}{RSm} \quad (2)$$

Rc is the average height of roughness curve elements, and Ra is the arithmetic average roughness. These parameters are measured in accordance with the regulations in JIS B 0601: 2001 (ISO 4287: 1997). Since the average height Rc of roughness curve elements is the average of roughness heights in a profile curve, the prominent peak projected area A may be calculated by the following procedures using the roughness height Rc, RSm and the viscous sublayer height δs.

As illustrated in FIG. 4, the prominent peak projected area a of a single peak standing out above the viscous sublayer, assuming that the peak is a circular cone, is obtained as the area of a triangle defined by the height h and the base l. Thus, the projected area is calculated using $0.5 \times h \times l$ as shown in Equation (3). Because l can be represented using x in FIG. 4 as RSm−2x, and h can be represented as Rc−δs, Equation (3) can be transformed through the procedures (3) to (9) using Rc and RSm into the final form (9). As shown in (11), the prominent peak projected area A is calculated as the product of the prominent peak projected area a of a single peak standing out above the viscous sublayer, multiplied by the number N of peaks per unit area calculated from Equation (10).

[Math. 9]

$$a = 0.5 \times h \times l \quad (3)$$

[Math. 10]

$$h = Rc - \delta s \quad (4)$$

[Math. 11]

$$l = RSm - 2x \quad (5)$$

[Math. 12]

$$\tan\theta = \frac{Rc}{\frac{1}{2}RSm} = \frac{\delta s}{x} \quad (6)$$

[Math. 13]

$$x = \frac{\frac{1}{2}RSm \times \delta s}{Rc} \quad (7)$$

[Math. 14]

$$l = RSm - \frac{RSm \times \delta s}{Rc} = \frac{RSm \times Rc - RSm \times \delta s}{Rc} = \frac{RSm \times (Rc - \delta s)}{Rc} \quad (8)$$

[Math. 15]

$$a = 0.5 \times h \times l = \\ 0.5 \times (Rc - \delta s) \frac{RSm \times Rc - RSm \times \delta s}{Rc} = 0.5 \times \frac{RSm \times (Rc - \delta s)^2}{Rc} \quad (9)$$

[Math. 16]

$$N = \frac{1}{RSm^2} (/m^2) \quad (10)$$

[Math. 17]

$$A = a \times N = 0.5 \times \frac{RSm \times (Rc - \delta s)^2}{Rc} \times \frac{1}{RSm^2} = 0.5 \times \frac{(Rc - \delta s)^2}{RSm} (m^2) \quad (11)$$

Ra is the arithmetic average roughness and is a value obtained by folding the roughness curve f(x) along the mean line and dividing the area defined by the roughness curve and the mean line with the length, as shown in Equation (12). Thus, this parameter can be regarded as the projected area per unit length. Therefore, as shown in Equation (13), the subtraction of δs produces the projected area a of prominent roughness standing out above the viscous sublayer.

As shown in Equation (14), the number N of such projected areas per unit length that are found per unit area is indicated by 1/RSm similarly to Equation (10). Thus, the prominent peak projected area A is calculated as shown in Equation (15).

[Math. 18]
$$Ra = \frac{1}{l}\int_0^l |f(x)| dx \quad (12)$$

[Math. 19]
$$a = Ra - \delta s \quad (13)$$

[Math. 20]
$$N = \frac{1}{RSm}(/m^2) \quad (14)$$

[Math. 21]
$$A = a \times N = \frac{(Ra - \delta s)}{RSm}(m^2) \quad (15)$$

Measurement of Roughness

The roughness may be measured or evaluated with a surface roughness meter such as a contact or non-contact, manual or automatic type. A stylus profilometer or a laser displacement meter is generally used and is advantageous in aspects such as simplicity. In particular, a laser displacement meter such as one using a line laser (Ultra-High Speed In-line Profilometer LJ-V7000 Series) can perform three-dimensional measurement quickly. The data obtained may be stored or may be analog/digital processed within the displacement meter.

In the parameter analysis, it is desired to use the profile curve as such. When, however, the influence of waviness of 10,000 µm and higher wavelengths is not negligible, the roughness curve may be measured while using a high-pass filter having a cut-off value (wavelength) λc of not less than 10,000 µm in accordance with JIS B 0601: 2001 (ISO 4287: 1997).

In the present invention, the evaluation length and the cut-off value λc which are necessary to evaluate the roughness accurately are not less than 10,000 µm, and the measurement pitches are not more than 500 µm. When the measurement pitches are 500 µm, the minimum wavelength that can be measured is 2,000 µm but the measurement results of low-wavelength roughness come to have a large margin of error. In view of this, the practical measurement pitches are about 250 µm. Reducing the measurement pitches leads to an increase in measurement time and also causes the measurement results to be affected by wavelengths of low roughness height which do not play a part in increasing the frictional resistance. In view of this, the practical measurement pitches are appropriately not less than 50 µm. When roughness with short wavelength is measured with an apparatus having long measurement pitches (a low resolution), some peaks are lost and the measurement may estimate the roughness height as being lower and the wavelength as being larger than they really are. It is therefore desirable to change the measurement pitches (the resolution) in accordance with the wavelength of the roughness of interest.

Calculation of Friction Increase Ratio FIR (%)

When the resistance due to friction with water stream is to be measured, the frictional resistance test may be performed by any of a towing test, a circular tube test, a double cylinder test and a cavitation tank test. In the case where a double cylinder device is used, the outer cylinder is rotated at a rotational speed of 500 rpm to 1000 rpm, and a torque which works on an inner specular cylinder is measured beforehand while increasing the rotational speed by 50 rpm. The frictional resistance $\tau_0$ (N/m$^2$) of the smooth surface per unit area is thus determined. Next, a cylinder with a rough surface is caused to rotate under the same conditions, and the frictional resistance $\tau_r$ (N/m$^2$) of the rough surface is determined at the respective rotational speeds. The friction increase ratio FIR (%) is calculated using Equation (16).

[Math. 22]
$$FIR\ (\%) = \frac{\tau_r - \tau_0}{\tau_0} \times 100 \quad (16)$$

The thickness of the viscous sublayer δs at each speed is measured by the frictional resistance test with respect to the smooth surface. Specifically, the frictional velocity u* is calculated from the frictional resistance $\tau_0$ of the smooth surface at each speed using Equation (17), δs is calculated from Equation (18) using the dimensionless distance y$^+$ (2<y$^+$<8) and the kinematic viscosity coefficient ν of the fluid of interest, and, from among the values of δs thus calculated, the value which provides a high coefficient of correlation between FIR (%) or Δτ and the prominent peak projected area A in Equation (19) or (24) described later is selected.

[Math. 23]
$$u^* = \sqrt{\frac{\tau_0}{\rho}} \quad (17)$$

[Math. 24]
$$\delta s = \frac{y^+ \times \nu}{u^*} \quad (18)$$

Here, u* is the frictional velocity, y$^+$ the dimensionless distance (y$^+$=2 to 8), ν the kinematic viscosity coefficient, and ρ the fluid density.

Determination of Coefficient C

[Math. 25]
$$FIR\ (\%) = C \times A \quad (19)$$

The slope C in Equation (19) varies depending on the type of roughness height R and the frictional resistance test method. Rough surfaces differing in the degree of roughness are prepared beforehand, and their frictional resistances are evaluated by a frictional resistance test while changing the flow velocity. The constant C in Equation (19) is determined from the relationship between the prominent peak projected area (A) and the FIR (%) thus measured.

When, for example, Rc and RSm are measured over an evaluation length of 30 mm and the frictional resistance test is performed using a double cylinder device, the coefficient C calculated using the prominent peak projected area A is 1274. When Ra and RSm are measured over an evaluation length of 30 mm and the frictional resistance test is performed using a double cylinder device, the coefficient is 1800.

From the foregoing, the frictional performance of a rough surface can be estimated by measuring Rc or Ra and further the average length RSm of roughness curve elements with respect to the rough surface, calculating the prominent peak projected area A using the viscous sublayer thickness $\delta s$ measured on a smooth surface at the flow velocity of interest, and predicting the friction increase ratio FIR (%) from Equation (19) using a constant C previously determined.

Calculation of Roughness Resistance Coefficient

In general, the drag (F) of a fluid is said to be proportional to the projected area S, the fluid density $\rho$ and the flow velocity V, and the coefficient $C_D$ of drag acting on roughness may be calculated as shown in Equation (20). The frictional resistance increase $\Delta \tau$ due to roughness is calculated using Equation (21), and, assuming that $\Delta \tau$ is the drag F, the frictional resistance coefficient $C_r$ of the roughness is calculated from Equation (22) using the flow velocity V, the fluid density $\rho$ and the prominent peak projected area A. In the case of a double cylinder test, the calculation of the flow velocity is simplified as shown in Equation (23) assuming that the flow velocity is decreased by half at the center between the outer cylinder and the inner cylinder. The flow velocity, however, can be calculated by other method that is selected appropriately in accordance with the manner in which the frictional resistance test is performed.

[Math. 26]
$$C_D = \frac{F}{\frac{1}{2}\rho S V^2} \quad (20)$$

[Math. 27]
$$\Delta \tau = \tau_r - \tau_0 \quad (21)$$

[Math. 28]
$$C_r = \frac{\Delta t}{\frac{1}{2}\rho A V^2} \quad (22)$$

[Math. 29]
$$V = \frac{1}{2}\pi D R \frac{1}{60} (m/s) \quad (23)$$

D: outer cylinder diameter
R(m): rotational speed (rpm)

Estimation of Frictional Resistance Increase $\Delta \tau$ (N/m$^2$) Due to Roughness Using Roughness Resistance Coefficient $C_r$ By using the roughness resistance coefficient $C_r$ calculated beforehand, the prominent peak projected area A, the fluid density and the flow velocity V, the frictional resistance increase $\Delta \tau$ (N/m$^2$) due to roughness can be calculated using Equation (24). The friction performance of the rough surface can be thus evaluated.

[Math. 30]
$$\Delta \tau = C_r \frac{1}{2}\rho A V^2 (N/m^2) \quad (24)$$

A surface performance estimating apparatus of the present invention uses the prediction method described hereinabove. The apparatus includes a measurement section configured to measure the roughness height R and the average length RSm of roughness curve elements, and a frictional resistance calculation unit configured to calculate the prominent peak projected area A using Equations (2) and (3) and to calculate the friction increase ratio FIR (%) using Equation (19) or the frictional resistance increase $\Delta \tau$ (N/m$^2$) due to roughness using Equation (24). With this surface evaluation apparatus, the friction increase ratio of a rough surface can be predicted easily and the surface performance can be estimated.

EXAMPLES

The present invention will be described in greater detail based on Examples hereinbelow. However, the scope of the invention is not limited to such Examples.

Example 1

Double Cylinder Test and Prominent Peak Projected Area A=0.5×(Rc−$\delta$s)$^2$/(Rc×RSm)

With a double cylinder device, the prominent peak projected area A was calculated from the average element height Rc, the average length RSm of roughness curve elements and the viscous sublayer thickness $\delta$s, and the relationship thereof with the friction increase ratio FIR (%) was evaluated.

To obtain sufficient accuracy, the surface roughness of the inner cylinder on which a coating had been formed was analyzed with respect to 58 lines with use of a laser displacement meter, starting from 5 mm above the bottom of the test piece to the top of the test piece at intervals of 5 mm. The displacement data was obtained for every 250 μm over a length of 1,000 mm, namely, 4,000 points of data were obtained. The measurement pitches were thus 250 μm. The data measured with respect to one line was divided into 33 segments each corresponding to an evaluation length of 30 mm, and thereafter an approximate curve obtained by a mean square method was subtracted. A profile curve was thus obtained. Fifteen test inner cylinders A to O were provided.

In actual evaluation, a roughness curve is desirably obtained while using a low-pass filter having a cut-off wavelength $\lambda$s in order to remove the waviness influence due to long wavelengths. Here, because the cylinders used had been processed by a high-precision technique and had no waviness influence due to long wavelengths, the profile curve was evaluated as such.

From the profile curve, Rz (the highest roughness), Rzjis (the ten point average roughness), Rc (the average height of roughness curve elements), Ra (the arithmetic average roughness), Rq (the root mean square roughness) and RSm were calculated.

Table 1 describes the results of Rz, Rzjis, Rc, Ra, Rq, Rsk, Rku and RSm measured with a double cylinder device which included any of the cylinders A to O. The cylinder A alone had extremely small wavelengths and the roughness was so small for 250 μm pitches that the wavelengths were measured to be longer than they really were; the results thereof described in Table 1 are values obtained by remeasurement with respect to one region 30 mm×30 mm with use of a laser displacement meter having measurement pitches of 50 μm.

The double cylinder device was such that a stainless steel tank (an outer cylinder, $\phi$ 320 mm diameter) was filled with seawater (23° C., density $\rho$=1023.95 (kg/m$^3$), kinematic viscosity 9.9812×10$^{-7}$ (m$^2$/s)), and a vinyl chloride test cylinder ($\phi$ 310 mm×H 300 mm) whose surface had been roughened by spraying of a paint thereto was placed therein. The outer cylinder was rotated at 500 rpm to 1000 rpm, and the torque which worked on the coated rough inner cylinder was measured sequentially at the respective rotational speeds. Because a variation in the thickness of the coatings formed on the coated cylinders would give rise to changes in frictional resistance $\tau_0$ (N/m$^2$) and viscous sublayer thickness offered by smooth surfaces, a smooth cylinder ($\phi$ 311 mm×H 300 mm) was provided as a cylinder having a film thickness of 500 μm and the torque which worked thereon was measured, and another smooth cylinder ($\phi$ 309 mm×H 300 mm) was provided as a cylinder having a film thickness of −500 μm and the torque which worked thereon was measured. The frictional resistance $\tau_0$ of the smooth surface and the viscous sublayer thickness were corrected as if the thickness of the corresponding coating had been added. Table 2 describes the frictional resistance $\tau_0$ of the smooth surface of each of the cylinders after the correction based on film thickness. Table 3 describes the frictional resistance $\tau_r$ of the rough surface of each of the cylinders.

The friction increase ratios FIR (%) of the roughened inner cylinders at 500 to 1000 (rpm) were calculated using Equation (16), the results being described in Table 4. In this example, the viscous sublayer thickness δs was calculated using Equations (17) and (18) assuming that the dimensionless distance (y$^+$) was 4.0, the results being described in Table 5. Using the viscous sublayer thickness δs in Table 5 and the average element height Rc of each cylinder described in Table 1, the prominent peak projected area A was calculated from Equation (1), the results being described in Table 6. The graph in FIG. 1 plots the prominent peak projected area A in Table 6 on the abscissa and the FIR (%) in Table 4 on the ordinate. C=1274.

An example of resistance prediction using this example will be described below.

Provided that the viscous sublayer thickness δs of the fluid of interest is 10 μm (dimensionless distance y$^+$=4.0), Rc is 40 μm and the wavelength is 3000 μm, the prominent peak projected area A calculated from Equation (1) is 0.0075 (m$^2$). Because C=1274, the FIR (%) is calculated to be 9.6% from Equation (19).

Example 2

Frictional Resistance Test Prominent Peak Projected Area A=(Ra−δs)/RSm

The frictional resistance measurement method and the roughness measurement method are the same as described in [Example 1]. In this example, the viscous sublayer thickness δs was calculated using Equations (17) and (18) assuming that the dimensionless distance (y$^+$) was 2.5, the results being described in Table 7. Using the viscous sublayer thickness δs in Table 7 and the average element height Ra of each cylinder described in Table 1, the prominent peak projected area A was calculated from Equation (2), the results being described in Table 8.

The graph in FIG. 2 plots the prominent peak projected area A in Table 8 on the abscissa and the FIR (%) in Table 4 on the ordinate. C=1800.

An example of resistance prediction using this example will be described below.

Provided that the viscous sublayer thickness δs of the fluid of interest is 6.5 μm (dimensionless distance y$^+$=2.5), Ra is 20 μm and the wavelength is 3000 μm, the prominent peak projected area A calculated from Equation (2) is 0.0045 (m$^2$). Because C=1800, the FIR (%) is calculated to be 8.1% from Equation (19).

Example 3

Regarding the roughness parameters of the cylinders described in Table 1, the correlations between any of Rz, Ra, Rq and Rzjis, and Rc are shown in FIG. 5, and the correlations between any of Rz, Rc, Rq and Rzjis, and Ra are shown in FIG. 6. The high correlations in all the cases show that any roughness height R may be used for the evaluation. Based on the results, when Rz, Rzjis or Rq is used as the roughness height R, the parameter R may be used in the calculation of the projected area with Equation (1) or Equation (2) after being converted using the slope a or a' of the parameter and Rc or Ra into:

$$Rc = a \times R \text{ or } Ra = a' \times R$$

Example 4

Using the flow velocity V, the fluid density $\rho$ and the prominent peak projected area A in Table 6 calculated in [Example 1], 0.5×fluid density $\rho$×prominent peak projected area A×squared flow velocity V was calculated, the results being described in Table 10. Here, the flow velocity V, shown in an upper row in Table 10, is a value obtained by simplified calculation with Equation (23) assuming that the flow velocity in the case of a double cylinder test would be decreased by half at the center between the outer cylinder and the inner cylinder. FIG. 7 shows a graph plotting the product of 0.5×fluid density $\rho$×prominent peak projected area A×squared flow velocity V described in Table 10 on the abscissa and Δτ in Table 9 on the ordinate. $C_r$=0.0556.

An example of resistance prediction using this example will be described below.

Provided that the fluid of interest has a density $\rho$=1023.95 (kg/m$^3$) and flows at a velocity of 8.4 (m/sec), the viscous sublayer thickness δs is 10 μm (dimensionless distance y$^+$=4.0), Rc is 40 μm and the wavelength is 3000 μm, the prominent peak projected area A calculated from Equation (2) is 0.0075 (m$^2$). Because $C_r$=0.0556, the frictional resistance increase Δτ is calculated to be 15 (N/m$^2$) from Equation (24).

Example 5

Using the frictional resistance $\tau_0$ of the smooth surface described in Table 2 and the frictional resistance $\tau_r$ of the rough surface described in Table 3, the frictional resistance increase Δτ (N/m$^2$) of the rough surface compared to the smooth surface was calculated from Equation (21), the results being described in Table 9. Using the flow velocity V, the fluid density $\rho$ and the prominent peak projected area A in Table 8 calculated in [Example 2], 0.5×fluid density $\rho$×prominent peak projected area A×squared flow velocity V was calculated, the results being described in Table 11. Here, the flow velocity V, shown in an upper row in Table 11, is a value obtained by simplified calculation with Equation (23) assuming that the flow velocity V in the case of a double cylinder test would be decreased by half at the center between the outer cylinder and the inner cylinder. FIG. 8 shows a graph plotting the product of 0.5×fluid density $\rho$×prominent peak projected area A×squared flow velocity V described in Table 11 on the abscissa and Δτ in Table 9 on the ordinate. $C_r$=0.0782.

An example of resistance prediction using this example will be described below.

Provided that the fluid of interest has a density $\rho=1023.95$ (kg/m$^3$) and flows at a velocity of 8.4 (m/sec), the viscous sublayer thickness $\delta s$ of the fluid of interest is 6.5 µm (dimensionless distance $y^+=2.5$), Ra is 20 µm and the wavelength is 3000 µm, the total prominent peak projected area A per unit area calculated from Equation (2) is 0.0045 (m$^2$). Because $C_r=0.0782$, the frictional resistance increase $\Delta\tau$ is calculated to be 12.7 (N/m$^2$) from Equation (24).

Example 6

FIG. 9 illustrates an example surface roughness measuring apparatus which includes LJ-V7080 manufactured by KEYENCE CORPORATION as a measurement section of a displacement meter using a two-dimensional beam line laser, and optical scale sensor VP-90 manufactured by KEYENCE CORPORATION as a travel distance reading section. With use of a scale attached to a wheel, the optical scale sensor can record displacements at measurement pitches of about 50 µm and can output data as three-dimensional shapes. With this configuration, a three-dimensional measurement apparatus capable of quick measurement of surface roughness can be realized. According to this configuration, the projected area and number of roughness in the flowing direction can be measured at the same time, and the prominent peak projected area A can be determined very quickly. Data for resistance prediction can be thus obtained.

TABLE 1

Results of measurement of roughness parameters

| Cylinders Nos. | Film thickness (µm) | Rz (µm) | Rzjis (µm) | Rc (µm) | Ra (µm) | Rq (µm) | Rsk | Rku | RSm (µm) |
|---|---|---|---|---|---|---|---|---|---|
| A | 262 | 166.9 | 134.1 | 64.8 | 22.9 | 28.9 | 0.2 | 3.1 | 998 |
| B | 321 | 256.9 | 133.1 | 148.3 | 51.0 | 63.3 | 0.5 | 3.0 | 5604 |
| C | 242 | 149.9 | 105.7 | 76.3 | 26.7 | 32.8 | 0.1 | 2.7 | 3214 |
| D | 324 | 156.9 | 105.4 | 77.6 | 27.0 | 33.6 | 0.2 | 2.9 | 3404 |
| E | 219 | 140.1 | 97.8 | 68.2 | 24.0 | 29.8 | 0.2 | 2.9 | 3042 |
| F | 309 | 144.9 | 96.4 | 71.4 | 25.3 | 31.4 | 0.2 | 2.9 | 3449 |
| G | 257 | 134.6 | 92.9 | 65.4 | 23.2 | 28.8 | 0.2 | 2.9 | 3112 |
| H | 216 | 117.7 | 78.1 | 55.1 | 19.1 | 24.3 | 0.6 | 3.5 | 3057 |
| I | 391 | 104.1 | 57.0 | 55.2 | 19.7 | 24.4 | 0.3 | 2.9 | 5111 |
| J | 454 | 84.0 | 53.9 | 41.6 | 14.7 | 18.3 | 0.2 | 3.0 | 3777 |
| K | 311 | 75.2 | 47.1 | 35.0 | 12.4 | 15.9 | 0.6 | 3.7 | 3523 |
| L | 484 | 75.0 | 46.9 | 36.9 | 13.1 | 16.3 | 0.2 | 3.0 | 3910 |
| M | 46 | 62.0 | 40.8 | 28.2 | 10.3 | 13.0 | 0.3 | 3.2 | 3095 |
| N | 140 | 50.4 | 32.5 | 23.5 | 8.7 | 10.9 | 0.3 | 3.1 | 3385 |
| O | 283 | 38.7 | 18.6 | 20.9 | 7.8 | 9.6 | 0.1 | 2.8 | 6063 |

The roughness was measured at measurement pitches of 50 µm for Cylinder A and at measurement pitches of 250 µm for Cylinders B to O.

TABLE 2

Frictional resistance $\tau_0$ of smooth surface of cylinders (corrected based on film thickness)

Frictional resistance $\tau_0$ of smooth surface (N/m$^2$)

| (rpm) | 1000 | 950 | 900 | 850 | 800 | 750 | 700 | 650 | 600 | 550 | 500 |
|---|---|---|---|---|---|---|---|---|---|---|---|
| A | 150.1 | 137.2 | 124.9 | 113.0 | 101.2 | 90.2 | 80.1 | 70.2 | 60.9 | 52.4 | 44.5 |
| B | 150.5 | 137.5 | 125.2 | 113.3 | 101.5 | 90.5 | 80.4 | 70.4 | 61.1 | 52.6 | 44.6 |
| C | 149.9 | 137.0 | 124.7 | 112.9 | 101.1 | 90.2 | 80.0 | 70.1 | 60.9 | 52.4 | 44.4 |
| D | 150.5 | 137.5 | 125.2 | 113.3 | 101.5 | 90.5 | 80.4 | 70.4 | 61.1 | 52.6 | 44.6 |
| E | 149.7 | 136.9 | 124.6 | 112.7 | 101.0 | 90.0 | 79.9 | 70.0 | 60.8 | 52.3 | 44.4 |
| F | 150.4 | 137.4 | 125.1 | 113.3 | 101.4 | 90.5 | 80.3 | 70.4 | 61.0 | 52.5 | 44.6 |
| G | 150.0 | 137.1 | 124.8 | 113.0 | 101.2 | 90.2 | 80.1 | 70.2 | 60.9 | 52.4 | 44.5 |
| H | 149.7 | 136.8 | 124.6 | 112.7 | 101.0 | 90.0 | 79.9 | 70.0 | 60.8 | 52.3 | 44.4 |
| I | 151.0 | 138.0 | 125.6 | 113.7 | 101.8 | 90.8 | 80.6 | 70.7 | 61.3 | 52.7 | 44.7 |
| J | 151.4 | 138.3 | 126.0 | 114.0 | 102.1 | 91.1 | 80.8 | 70.9 | 61.4 | 52.9 | 44.8 |
| K | 150.4 | 137.5 | 125.2 | 113.3 | 101.4 | 90.5 | 80.3 | 70.4 | 61.1 | 52.5 | 44.6 |
| L | 151.6 | 138.5 | 126.2 | 114.2 | 102.2 | 91.2 | 80.9 | 71.0 | 61.5 | 52.9 | 44.9 |
| M | 148.4 | 135.7 | 123.4 | 111.6 | 100.0 | 89.2 | 79.2 | 69.3 | 60.2 | 51.8 | 44.0 |
| N | 149.2 | 136.3 | 124.1 | 112.2 | 100.6 | 89.7 | 79.6 | 69.7 | 60.5 | 52.1 | 44.2 |
| O | 150.2 | 137.3 | 125.0 | 113.1 | 101.3 | 90.3 | 80.2 | 70.3 | 61.0 | 52.5 | 44.5 |

TABLE 3

Frictional resistance $\tau_r$ of rough surface of cylinders

Frictional resistance $\tau_r$ of rough surface (N/m²)

| (rpm) | 1000 | 950 | 900 | 850 | 800 | 750 | 700 | 650 | 600 | 550 | 500 |
|---|---|---|---|---|---|---|---|---|---|---|---|
| A | 191.0 | 173.9 | 156.7 | 141.3 | 126.3 | 111.8 | 98.5 | 86.1 | 74.0 | 63.2 | 53.1 |
| B | 172.0 | 157.0 | 143.1 | 128.7 | 115.4 | 102.9 | 91.0 | 79.5 | 69.0 | 58.9 | 49.9 |
| C | 165.6 | 151.3 | 137.5 | 123.9 | 111.1 | 98.4 | 87.3 | 76.2 | 66.0 | 56.4 | 47.7 |
| D | 165.9 | 151.8 | 137.9 | 124.3 | 111.3 | 99.3 | 87.5 | 76.3 | 66.1 | 56.3 | 47.7 |
| E | 167.6 | 152.8 | 138.9 | 124.7 | 111.9 | 99.2 | 87.6 | 76.5 | 66.2 | 56.7 | 47.7 |
| F | 168.1 | 153.0 | 138.6 | 125.0 | 111.8 | 99.3 | 87.6 | 76.6 | 66.3 | 56.7 | 47.9 |
| G | 170.3 | 155.0 | 140.9 | 127.0 | 113.5 | 100.7 | 88.9 | 77.9 | 67.3 | 57.5 | 48.7 |
| H | 166.0 | 150.9 | 137.0 | 123.9 | 110.3 | 97.8 | 86.8 | 75.7 | 65.2 | 56.0 | 47.3 |
| I | 157.1 | 143.4 | 130.5 | 117.5 | 105.6 | 94.3 | 83.1 | 72.8 | 63.2 | 53.9 | 45.6 |
| J | 158.0 | 144.2 | 131.2 | 118.3 | 106.1 | 94.7 | 83.8 | 73.4 | 63.8 | 54.9 | 46.4 |
| K | 158.2 | 144.6 | 130.9 | 118.1 | 105.8 | 94.6 | 83.2 | 72.6 | 63.2 | 54.0 | 45.8 |
| L | 158.2 | 144.5 | 131.2 | 118.7 | 106.4 | 95.1 | 83.9 | 73.6 | 63.7 | 54.7 | 46.4 |
| M | 153.3 | 139.9 | 127.3 | 115.0 | 102.7 | 91.8 | 81.0 | 70.8 | 61.4 | 52.7 | 44.5 |
| N | 152.5 | 139.3 | 126.8 | 114.2 | 102.4 | 91.0 | 80.7 | 70.8 | 61.2 | 52.3 | 44.5 |
| O | 152.9 | 139.7 | 127.2 | 115.0 | 103.6 | 92.1 | 81.1 | 71.6 | 61.8 | 53.2 | 45.0 |

TABLE 4

Friction increase ratio FIR (%) of coated cylinders

FIR (%)

| (rpm) | 1000 | 950 | 900 | 850 | 800 | 750 | 700 | 650 | 600 | 550 | 500 |
|---|---|---|---|---|---|---|---|---|---|---|---|
| A | 27.3 | 26.8 | 25.5 | 25.1 | 24.8 | 23.9 | 22.9 | 22.6 | 21.4 | 20.6 | 19.4 |
| B | 14.3 | 14.2 | 14.3 | 13.6 | 13.8 | 13.6 | 13.3 | 12.8 | 12.9 | 12.1 | 11.8 |
| C | 10.5 | 10.4 | 10.2 | 9.8 | 9.9 | 9.1 | 9.1 | 8.7 | 8.4 | 7.7 | 7.2 |
| D | 10.2 | 10.3 | 10.1 | 9.6 | 9.6 | 9.7 | 8.8 | 8.4 | 8.3 | 7.1 | 6.9 |
| E | 11.9 | 11.6 | 11.5 | 10.7 | 10.8 | 10.2 | 9.5 | 9.2 | 8.9 | 8.4 | 7.4 |
| F | 11.8 | 11.3 | 10.8 | 10.3 | 10.2 | 9.8 | 9.1 | 8.8 | 8.5 | 7.9 | 7.4 |
| G | 13.5 | 13.0 | 12.9 | 12.4 | 12.2 | 11.6 | 11.0 | 11.0 | 10.4 | 9.8 | 9.5 |
| H | 10.9 | 10.2 | 10.0 | 9.9 | 9.3 | 8.6 | 8.6 | 8.1 | 7.3 | 7.1 | 6.6 |
| I | 4.0 | 3.9 | 3.9 | 3.3 | 3.7 | 3.9 | 3.1 | 3.0 | 3.2 | 2.2 | 1.9 |
| J | 4.4 | 4.2 | 4.2 | 3.7 | 3.9 | 4.0 | 3.6 | 3.6 | 3.9 | 3.8 | 3.5 |
| K | 5.2 | 5.2 | 4.6 | 4.3 | 4.3 | 4.5 | 3.6 | 3.2 | 3.6 | 2.9 | 2.6 |
| L | 4.3 | 4.3 | 4.0 | 3.9 | 4.0 | 4.3 | 3.6 | 3.7 | 3.7 | 3.3 | 3.4 |
| M | 3.3 | 3.1 | 3.1 | 3.0 | 2.7 | 2.9 | 2.3 | 2.1 | 2.0 | 1.8 | 1.3 |
| N | 2.2 | 2.2 | 2.2 | 1.7 | 1.8 | 1.4 | 1.3 | 1.5 | 1.0 | 0.3 | 0.8 |
| O | 1.8 | 1.7 | 1.8 | 1.7 | 2.3 | 1.9 | 1.1 | 1.9 | 1.3 | 1.5 | 1.1 |

TABLE 5

Viscous sublayer thickness δs ($y^+ = 4$) of cylinders

δs ($y^+ = 4$) (μm)

| (rpm) | 1000 | 950 | 900 | 850 | 800 | 750 | 700 | 650 | 600 | 550 | 500 |
|---|---|---|---|---|---|---|---|---|---|---|---|
| A | 10.43 | 10.91 | 11.43 | 12.02 | 12.70 | 13.45 | 14.27 | 15.24 | 16.37 | 17.64 | 19.15 |
| B | 10.41 | 10.89 | 11.42 | 12.00 | 12.68 | 13.43 | 14.25 | 15.22 | 16.34 | 17.62 | 19.12 |
| C | 10.43 | 10.91 | 11.44 | 12.02 | 12.71 | 13.45 | 14.28 | 15.25 | 16.37 | 17.65 | 19.16 |
| D | 10.41 | 10.89 | 11.42 | 12.00 | 12.68 | 13.43 | 14.25 | 15.22 | 16.34 | 17.62 | 19.12 |
| E | 10.44 | 10.92 | 11.45 | 12.03 | 12.71 | 13.46 | 14.29 | 15.26 | 16.38 | 17.66 | 19.17 |
| F | 10.42 | 10.90 | 11.42 | 12.00 | 12.68 | 13.43 | 14.25 | 15.23 | 16.35 | 17.62 | 19.13 |
| G | 10.43 | 10.91 | 11.43 | 12.02 | 12.70 | 13.45 | 14.27 | 15.25 | 16.37 | 17.65 | 19.15 |
| H | 10.44 | 10.92 | 11.45 | 12.03 | 12.71 | 13.46 | 14.29 | 15.26 | 16.39 | 17.67 | 19.17 |
| I | 10.40 | 10.88 | 11.40 | 11.98 | 12.66 | 13.40 | 14.23 | 15.19 | 16.32 | 17.59 | 19.09 |
| J | 10.38 | 10.86 | 11.38 | 11.96 | 12.64 | 13.38 | 14.21 | 15.17 | 16.30 | 17.56 | 19.07 |
| K | 10.42 | 10.90 | 11.42 | 12.00 | 12.68 | 13.43 | 14.25 | 15.22 | 16.35 | 17.62 | 19.13 |
| L | 10.37 | 10.85 | 11.37 | 11.95 | 12.63 | 13.38 | 14.20 | 15.16 | 16.29 | 17.55 | 19.06 |
| M | 10.49 | 10.97 | 11.50 | 12.09 | 12.77 | 13.53 | 14.36 | 15.34 | 16.46 | 17.75 | 19.27 |
| N | 10.46 | 10.94 | 11.47 | 12.06 | 12.74 | 13.49 | 14.32 | 15.30 | 16.42 | 17.70 | 19.21 |
| O | 10.42 | 10.90 | 11.43 | 12.01 | 12.69 | 13.44 | 14.26 | 15.24 | 16.36 | 17.63 | 19.14 |

TABLE 6

Prominent peak projected area A = 0.5 × (Rc − (δs)²/(Rc × RSm) of cylinders

Prominent peak projected area A = 0.5 × (Rc − δs)²/(Rc × RSm) (m²)

| (rpm) | 1000 | 950 | 900 | 850 | 800 | 750 | 700 | 650 | 600 | 550 | 500 |
|---|---|---|---|---|---|---|---|---|---|---|---|
| A | 0.0229 | 0.0225 | 0.0220 | 0.0215 | 0.0210 | 0.0204 | 0.0197 | 0.0190 | 0.0181 | 0.0172 | 0.0161 |
| B | 0.0114 | 0.0114 | 0.0113 | 0.0112 | 0.0111 | 0.0109 | 0.0108 | 0.0107 | 0.0105 | 0.0103 | 0.0100 |
| C | 0.0088 | 0.0087 | 0.0086 | 0.0084 | 0.0082 | 0.0081 | 0.0078 | 0.0076 | 0.0073 | 0.0070 | 0.0067 |
| D | 0.0085 | 0.0084 | 0.0083 | 0.0081 | 0.0080 | 0.0078 | 0.0076 | 0.0074 | 0.0071 | 0.0068 | 0.0065 |
| E | 0.0080 | 0.0079 | 0.0078 | 0.0076 | 0.0074 | 0.0072 | 0.0070 | 0.0068 | 0.0065 | 0.0062 | 0.0058 |
| F | 0.0076 | 0.0074 | 0.0073 | 0.0072 | 0.0070 | 0.0068 | 0.0066 | 0.0064 | 0.0062 | 0.0059 | 0.0055 |
| G | 0.0074 | 0.0073 | 0.0072 | 0.0070 | 0.0068 | 0.0066 | 0.0064 | 0.0062 | 0.0059 | 0.0056 | 0.0053 |
| H | 0.0059 | 0.0058 | 0.0057 | 0.0055 | 0.0053 | 0.0051 | 0.0049 | 0.0047 | 0.0044 | 0.0042 | 0.0038 |
| I | 0.0036 | 0.0035 | 0.0034 | 0.0033 | 0.0032 | 0.0031 | 0.0030 | 0.0028 | 0.0027 | 0.0025 | 0.0023 |
| J | 0.0031 | 0.0030 | 0.0029 | 0.0028 | 0.0027 | 0.0025 | 0.0024 | 0.0022 | 0.0020 | 0.0018 | 0.0016 |
| K | 0.0025 | 0.0024 | 0.0023 | 0.0021 | 0.0020 | 0.0019 | 0.0017 | 0.0016 | 0.0014 | 0.0012 | 0.0010 |
| L | 0.0024 | 0.0024 | 0.0023 | 0.0022 | 0.0020 | 0.0019 | 0.0018 | 0.0016 | 0.0015 | 0.0013 | 0.0011 |
| M | 0.0018 | 0.0017 | 0.0016 | 0.0015 | 0.0014 | 0.0012 | 0.0011 | 0.0009 | 0.0008 | 0.0006 | 0.0005 |
| N | 0.0011 | 0.0010 | 0.0009 | 0.0008 | 0.0007 | 0.0006 | 0.0005 | 0.0004 | 0.0003 | 0.0002 | 0.0001 |
| O | 0.0004 | 0.0004 | 0.0004 | 0.0003 | 0.0003 | 0.0002 | 0.0002 | 0.0001 | 0.0001 | 0.0000 | 0.0000 |

TABLE 7

Viscous sublayer thickness δs of cylinders (Example 2)

δs (y$^+$ = 2.5) (μm)

| (rpm) | 1000 | 950 | 900 | 850 | 800 | 750 | 700 | 650 | 600 | 550 | 500 |
|---|---|---|---|---|---|---|---|---|---|---|---|
| A | 6.52 | 6.82 | 7.15 | 7.51 | 7.94 | 8.40 | 8.92 | 9.53 | 10.23 | 11.03 | 11.97 |
| B | 6.51 | 6.81 | 7.13 | 7.50 | 7.93 | 8.39 | 8.91 | 9.51 | 10.21 | 11.01 | 11.95 |
| C | 6.52 | 6.82 | 7.15 | 7.51 | 7.94 | 8.41 | 8.92 | 9.53 | 10.23 | 11.03 | 11.97 |
| D | 6.51 | 6.81 | 7.13 | 7.50 | 7.92 | 8.39 | 8.91 | 9.51 | 10.21 | 11.01 | 11.95 |
| E | 6.52 | 6.82 | 7.15 | 7.52 | 7.95 | 8.41 | 8.93 | 9.54 | 10.24 | 11.04 | 11.98 |
| F | 6.51 | 6.81 | 7.14 | 7.50 | 7.93 | 8.39 | 8.91 | 9.52 | 10.22 | 11.01 | 11.95 |
| G | 6.52 | 6.82 | 7.15 | 7.51 | 7.94 | 8.41 | 8.92 | 9.53 | 10.23 | 11.03 | 11.97 |
| H | 6.53 | 6.83 | 7.15 | 7.52 | 7.95 | 8.41 | 8.93 | 9.54 | 10.24 | 11.04 | 11.98 |
| I | 6.50 | 6.80 | 7.12 | 7.49 | 7.91 | 8.38 | 8.89 | 9.50 | 10.20 | 10.99 | 11.93 |
| J | 6.49 | 6.79 | 7.11 | 7.48 | 7.90 | 8.37 | 8.88 | 9.48 | 10.19 | 10.98 | 11.92 |
| K | 6.51 | 6.81 | 7.14 | 7.50 | 7.93 | 8.39 | 8.91 | 9.52 | 10.22 | 11.01 | 11.95 |
| L | 6.48 | 6.78 | 7.11 | 7.47 | 7.90 | 8.36 | 8.87 | 9.48 | 10.18 | 10.97 | 11.91 |
| M | 6.55 | 6.85 | 7.19 | 7.56 | 7.98 | 8.45 | 8.97 | 9.59 | 10.29 | 11.09 | 12.04 |
| N | 6.54 | 6.84 | 7.17 | 7.54 | 7.96 | 8.43 | 8.95 | 9.56 | 10.26 | 11.06 | 12.01 |
| O | 6.51 | 6.81 | 7.14 | 7.51 | 7.93 | 8.40 | 8.91 | 9.52 | 10.22 | 11.02 | 11.96 |

TABLE 8

Prominent peak projected area A = (Ra − δs)/RSm of cylinders (Example 2)

Prominent peak projected area A = (Ra − δs)/RSm (m²)

| (rpm) | 1000 | 950 | 900 | 850 | 800 | 750 | 700 | 650 | 600 | 550 | 500 |
|---|---|---|---|---|---|---|---|---|---|---|---|
| A | 0.0164 | 0.0161 | 0.0158 | 0.0154 | 0.0150 | 0.0145 | 0.0140 | 0.0134 | 0.0127 | 0.0119 | 0.0110 |
| B | 0.0079 | 0.0079 | 0.0078 | 0.0078 | 0.0077 | 0.0076 | 0.0075 | 0.0074 | 0.0073 | 0.0071 | 0.0070 |
| C | 0.0063 | 0.0062 | 0.0061 | 0.0060 | 0.0058 | 0.0057 | 0.0055 | 0.0053 | 0.0051 | 0.0049 | 0.0046 |
| D | 0.0060 | 0.0059 | 0.0058 | 0.0057 | 0.0056 | 0.0055 | 0.0053 | 0.0051 | 0.0049 | 0.0047 | 0.0044 |
| E | 0.0057 | 0.0056 | 0.0055 | 0.0054 | 0.0053 | 0.0051 | 0.0050 | 0.0048 | 0.0045 | 0.0043 | 0.0040 |
| F | 0.0054 | 0.0054 | 0.0053 | 0.0052 | 0.0050 | 0.0049 | 0.0048 | 0.0046 | 0.0044 | 0.0041 | 0.0039 |
| G | 0.0054 | 0.0053 | 0.0052 | 0.0050 | 0.0049 | 0.0048 | 0.0046 | 0.0044 | 0.0042 | 0.0039 | 0.0036 |
| H | 0.0041 | 0.0040 | 0.0039 | 0.0038 | 0.0036 | 0.0035 | 0.0033 | 0.0031 | 0.0029 | 0.0026 | 0.0023 |
| I | 0.0026 | 0.0025 | 0.0025 | 0.0024 | 0.0023 | 0.0022 | 0.0021 | 0.0020 | 0.0019 | 0.0017 | 0.0015 |
| J | 0.0022 | 0.0021 | 0.0020 | 0.0019 | 0.0018 | 0.0017 | 0.0015 | 0.0014 | 0.0012 | 0.0010 | 0.0007 |
| K | 0.0017 | 0.0016 | 0.0015 | 0.0014 | 0.0013 | 0.0011 | 0.0010 | 0.0008 | 0.0006 | 0.0004 | 0.0001 |
| L | 0.0017 | 0.0016 | 0.0015 | 0.0014 | 0.0013 | 0.0012 | 0.0011 | 0.0009 | 0.0007 | 0.0005 | 0.0003 |
| M | 0.0012 | 0.0011 | 0.0010 | 0.0009 | 0.0007 | 0.0006 | 0.0004 | 0.0002 | 0.0000 | −0.0003 | −0.0006 |
| N | 0.0006 | 0.0006 | 0.0005 | 0.0003 | 0.0002 | 0.0001 | −0.0001 | −0.0003 | −0.0005 | −0.0007 | −0.0010 |
| O | 0.0002 | 0.0002 | 0.0001 | 0.0000 | 0.0000 | −0.0001 | −0.0002 | −0.0003 | −0.0004 | −0.0005 | −0.0007 |

TABLE 9

Frictional resistance increase Δτ (N/m²)

Frictional resistance increase Δτ (N/m²)

| (rpm) | 1000 | 950 | 900 | 850 | 800 | 750 | 700 | 650 | 600 | 550 | 500 |
|---|---|---|---|---|---|---|---|---|---|---|---|
| A | 41.0 | 36.7 | 31.8 | 28.3 | 25.1 | 21.6 | 18.4 | 15.9 | 13.1 | 10.8 | 8.6 |
| B | 21.5 | 19.5 | 17.9 | 15.4 | 14.0 | 12.3 | 10.7 | 9.0 | 7.9 | 6.3 | 5.3 |
| C | 15.7 | 14.3 | 12.8 | 11.1 | 10.0 | 8.2 | 7.3 | 6.1 | 5.1 | 4.0 | 3.2 |
| D | 15.4 | 14.2 | 12.6 | 10.9 | 9.8 | 8.7 | 7.1 | 5.9 | 5.1 | 3.8 | 3.1 |
| E | 17.8 | 15.9 | 14.3 | 12.0 | 10.9 | 9.2 | 7.6 | 6.4 | 5.4 | 4.4 | 3.3 |
| F | 17.7 | 15.6 | 13.5 | 11.7 | 10.3 | 8.8 | 7.3 | 6.2 | 5.2 | 4.2 | 3.3 |
| G | 20.3 | 17.9 | 16.1 | 14.0 | 12.4 | 10.5 | 8.8 | 7.7 | 6.4 | 5.1 | 4.2 |
| H | 16.3 | 14.0 | 12.4 | 11.2 | 9.4 | 7.8 | 6.9 | 5.7 | 4.4 | 3.7 | 2.9 |
| I | 6.1 | 5.4 | 4.9 | 3.8 | 3.8 | 3.5 | 2.5 | 2.1 | 2.0 | 1.2 | 0.9 |
| J | 6.6 | 5.9 | 5.2 | 4.3 | 4.0 | 3.6 | 2.9 | 2.5 | 2.4 | 2.0 | 1.6 |
| K | 7.8 | 7.1 | 5.8 | 4.9 | 4.4 | 4.1 | 2.9 | 2.3 | 2.2 | 1.5 | 1.2 |
| L | 6.6 | 6.0 | 5.0 | 4.5 | 4.1 | 3.9 | 3.0 | 2.7 | 2.3 | 1.8 | 1.5 |
| M | 4.8 | 4.2 | 3.9 | 3.4 | 2.7 | 2.6 | 1.8 | 1.4 | 1.2 | 0.9 | 0.5 |
| N | 3.3 | 2.9 | 2.8 | 2.0 | 1.9 | 1.3 | 1.1 | 1.0 | 0.6 | 0.2 | 0.3 |
| O | 2.7 | 2.4 | 2.2 | 1.9 | 2.3 | 1.7 | 0.9 | 1.3 | 0.8 | 0.8 | 0.5 |

TABLE 10

Calculation of 0.5 × fluid density ρ × prominent peak projected area A × squared flow velocity V (Example 4)

$0.5 \times \rho \times A \times V^2$  A = $0.5 \times (Rc - \delta s)^2/(Rc \times RSm)$
(rpm)

| 1000 | 950 | 900 | 850 | 800 | 750 | 700 | 650 | 600 | 550 | 500 |
|---|---|---|---|---|---|---|---|---|---|---|
| | | | | | (m/sec) | | | | | |
| 8.4 | 8.0 | 7.5 | 7.1 | 6.7 | 6.3 | 5.9 | 5.4 | 5.0 | 4.6 | 4.2 |

| | 1000 | 950 | 900 | 850 | 800 | 750 | 700 | 650 | 600 | 550 | 500 |
|---|---|---|---|---|---|---|---|---|---|---|---|
| A | 821.6 | 728.5 | 641.2 | 559.4 | 482.8 | 412.3 | 347.7 | 288.4 | 234.7 | 187.0 | 144.8 |
| B | 411.1 | 368.4 | 328.1 | 290.2 | 254.5 | 221.2 | 190.4 | 161.8 | 135.5 | 111.7 | 90.2 |
| C | 317.8 | 282.7 | 249.7 | 218.7 | 189.6 | 162.8 | 138.1 | 115.4 | 94.7 | 76.2 | 59.8 |
| D | 307.0 | 273.1 | 241.3 | 211.5 | 183.5 | 157.6 | 133.8 | 111.8 | 91.9 | 74.0 | 58.1 |
| E | 288.9 | 256.4 | 225.9 | 197.4 | 170.6 | 146.0 | 123.3 | 102.5 | 83.7 | 66.9 | 52.0 |
| F | 271.3 | 241.0 | 212.6 | 186.0 | 161.0 | 137.9 | 116.7 | 97.3 | 79.6 | 63.8 | 49.8 |
| G | 266.7 | 236.6 | 208.2 | 181.7 | 156.9 | 134.0 | 113.1 | 93.8 | 76.4 | 60.9 | 47.2 |
| H | 212.7 | 187.9 | 164.6 | 142.9 | 122.6 | 104.0 | 87.1 | 71.5 | 57.6 | 45.2 | 34.4 |
| I | 127.8 | 112.9 | 99.0 | 86.0 | 73.8 | 62.6 | 52.4 | 43.1 | 34.7 | 27.2 | 20.8 |
| J | 111.4 | 97.5 | 84.6 | 72.6 | 61.4 | 51.2 | 42.0 | 33.7 | 26.4 | 20.0 | 14.5 |
| K | 88.1 | 76.4 | 65.6 | 55.7 | 46.4 | 38.1 | 30.7 | 24.1 | 18.3 | 13.3 | 9.2 |
| L | 87.6 | 76.2 | 65.7 | 56.0 | 46.9 | 38.8 | 31.4 | 24.9 | 19.0 | 14.1 | 9.9 |
| M | 64.6 | 55.2 | 46.5 | 38.6 | 31.4 | 24.9 | 19.3 | 14.4 | 10.2 | 6.8 | 4.1 |
| N | 38.4 | 32.2 | 26.5 | 21.4 | 16.7 | 12.7 | 9.3 | 6.4 | 4.1 | 2.3 | 1.0 |
| O | 15.6 | 12.8 | 10.3 | 8.1 | 6.1 | 4.4 | 3.1 | 1.9 | 1.1 | 0.5 | 0.1 |

TABLE 11

Calculation of 0.5 × fluid density ρ × prominent peak projected area A × squared flow velocity V (Example 5)

$0.5 \times \rho \times A \times V^2$  A = $(Ra - \delta s)/RSm$
(rpm)

| 1000 | 950 | 900 | 850 | 800 | 750 | 700 | 650 | 600 | 550 | 500 |
|---|---|---|---|---|---|---|---|---|---|---|
| | | | | | (m/sec) | | | | | |
| 8.4 | 8.0 | 7.5 | 7.1 | 6.7 | 6.3 | 5.9 | 5.4 | 5.0 | 4.6 | 4.2 |

| | 1000 | 950 | 900 | 850 | 800 | 750 | 700 | 650 | 600 | 550 | 500 |
|---|---|---|---|---|---|---|---|---|---|---|---|
| A | 590.1 | 522.8 | 459.6 | 400.5 | 344.9 | 293.7 | 246.8 | 203.5 | 164.3 | 129.4 | 98.4 |
| B | 285.3 | 255.8 | 227.8 | 201.5 | 176.8 | 153.7 | 132.3 | 112.4 | 94.2 | 77.6 | 62.6 |
| C | 225.6 | 200.6 | 177.0 | 155.0 | 134.2 | 115.0 | 97.4 | 81.1 | 66.3 | 53.0 | 41.2 |
| D | 216.3 | 192.4 | 169.9 | 148.7 | 128.9 | 110.5 | 93.6 | 78.0 | 63.8 | 51.1 | 39.7 |
| E | 206.4 | 183.1 | 161.2 | 140.6 | 121.4 | 103.6 | 87.2 | 72.2 | 58.5 | 46.3 | 35.5 |
| F | 195.8 | 173.8 | 153.3 | 134.0 | 115.8 | 99.1 | 83.7 | 69.5 | 56.6 | 45.0 | 34.8 |
| G | 192.6 | 170.7 | 150.1 | 130.9 | 112.8 | 96.1 | 80.8 | 66.7 | 53.9 | 42.5 | 32.4 |

TABLE 11-continued

Calculation of 0.5 × fluid density ρ × prominent peak projected area A × squared flow velocity V (Example 5)

| | \multicolumn{11}{c}{0.5 × ρ × A × V² A = (Ra − δs)/RSm} |
| | \multicolumn{11}{c}{(rpm)} |
| | 1000 | 950 | 900 | 850 | 800 | 750 | 700 | 650 | 600 | 550 | 500 |
| | \multicolumn{11}{c}{(m/sec)} |
| | 8.4 | 8.0 | 7.5 | 7.1 | 6.7 | 6.3 | 5.9 | 5.4 | 5.0 | 4.6 | 4.2 |
|---|---|---|---|---|---|---|---|---|---|---|---|
| H | 147.8 | 130.2 | 113.7 | 98.3 | 83.9 | 70.6 | 58.6 | 47.5 | 37.5 | 28.7 | 20.9 |
| I | 92.8 | 81.9 | 71.6 | 62.0 | 53.0 | 44.8 | 37.2 | 30.3 | 24.0 | 18.5 | 13.6 |
| J | 78.1 | 67.9 | 58.5 | 49.7 | 41.4 | 33.9 | 27.1 | 21.0 | 15.5 | 10.7 | 6.6 |
| K | 60.1 | 51.5 | 43.5 | 36.1 | 29.2 | 23.0 | 17.5 | 12.4 | 8.0 | 4.3 | 1.1 |
| L | 60.8 | 52.4 | 44.6 | 37.4 | 30.6 | 24.5 | 19.0 | 14.1 | 9.7 | 5.9 | 2.7 |
| M | 43.5 | 36.1 | 29.3 | 23.0 | 17.2 | 12.1 | 7.5 | 3.5 | 0.0 | −2.8 | −5.1 |
| N | 23.0 | 17.8 | 13.2 | 8.9 | 5.0 | 1.6 | −1.3 | −3.9 | −6.0 | −7.6 | −8.8 |
| O | 7.6 | 5.3 | 3.2 | 1.3 | −0.5 | −2.0 | −3.2 | −4.3 | −5.2 | −5.8 | −6.2 |

The invention claimed is:

1. A method for predicting frictional resistance of a rough surface having a variation in roughness wavelength and being in contact with a fluid flowing at varied velocities, the method comprising:

measuring roughness of the rough surface with a surface roughness meter, determining a prominent peak projected area A of the rough surface, which is a total projected area of all prominent peaks standing out above a viscous sublayer thickness per unit area, based on the measured roughness of the rough surface; and calculating a friction increase ratio FIR (%) using Equation (1) or a frictional resistance increase $\Delta\tau$ using Equation (2):

$$FIR(\%) = C \times A \quad (1)$$

$$\Delta\tau = C_r \frac{1}{2} \rho A V^2, \quad (2)$$

wherein in Equation (1), the coefficient C is a constant dependent on the prominent peak projected area A and is predetermined by performing a frictional resistance test beforehand in which frictional resistances are measured with respect to a plurality of rough surfaces having different degree of roughness while changing a flow velocity V and friction increase ratios FIR (%) of the plurality of rough surfaces are calculated, wherein the friction increase ratios FIR (%) are percentages of differences $\tau_r - \tau_0$ between frictional resistances $\tau_r$ of the plurality of rough surfaces and a frictional resistance $\tau_0$ of a smooth surface, divided by $\tau_0$, and in Equation (2), the coefficient $C_r$ is a constant dependent on a fluid density $\rho$, the prominent peak projected area A and the flow velocity V, and is predetermined from the relation of Equation (2) using values of frictional resistance increase $\Delta\tau$ obtained beforehand by a frictional resistance test in which frictional resistances are measured with respect to a plurality of rough surfaces having different degree of roughness while changing a flow velocity V, wherein the values of frictional resistance increase $\Delta\tau$ are differences $\tau_r - \tau_0$ between frictional resistances $\tau_r$ of the plurality of rough surfaces and a frictional resistance $\tau_0$ of a smooth surface.

2. The method according to claim 1, wherein the prominent peak projected area A is a value calculated using Equation (3) wherein RSm is an average length of roughness curve elements measured as roughness wavelength λ and Rc is an average height of roughness curve elements measured as roughness height R, in accordance with the regulations in ISO 4287: 1997 (JIS B 0601: 2001), $$A = 0.5 \times \frac{(Rc - \delta s)^2}{Rc \times RSm}, \quad (3)$$

wherein in Equation (3), δs is a viscous sublayer thickness measured by a frictional resistance test with respect to a smooth surface while changing a flow velocity V and is a value determined in such a manner that a frictional velocity u* is calculated from a frictional resistance $\tau_0$ of the smooth surface using Equation (5), δs is calculated from Equation (4) using a dimensionless distance $y^+(2<y^+<8)$ and a kinematic viscosity coefficient ν of a fluid of interest with respect to each of the varying flow velocity V, and, from among values of δs calculated from Equation (4) with respect to each of the varying flow velocity V, the value which provides a highest coefficient of correlation between FIR (%) or $\Delta\tau$ and the prominent peak projected area A in Equation (1) or (2) is selected as δs in Equation (3), $$\delta s = \frac{y^+ \times v}{u^*} \quad (4)$$

$$u^* \sqrt{\frac{\tau_0}{\rho}}. \quad (5)$$

3. The method according to claim 2, wherein the prominent peak projected area A is calculated in such a manner that highest roughness Rz, ten point average roughness Rzjis, root mean square roughness Rq or arithmetic average roughness Ra is measured as roughness height R', the slope a of the average height of roughness curve elements Rc to the measured parameter R' is determined, and the parameter R' is converted assuming that Rc=a×R' where R' is Rz, Rzjis, Rq or Ra.

4. The method according to claim 1, wherein the prominent peak projected area A is a value calculated using Equation (6) wherein RSm is an average length of roughness curve elements measured as roughness wavelength λ and Ra is an arithmetic average roughness measured as roughness height R, in accordance with the regulations in ISO 4287: 1997 (JIS B 0601: 2001)

$$A = \frac{(Ra - \delta s)}{RSm}, \quad (6)$$

wherein in Equation (6), δs is a viscous sublayer thickness measured by a frictional resistance test with respect to a smooth surface while changing a flow velocity V and is a value determined in such a manner that a frictional velocity u* is calculated from a frictional resistance $\tau_0$ of the smooth surface using Equation (5), δs is calculated from Equation (4) using a dimensionless distance $y^+$ ($2<y^+<8$) and a kinematic viscosity coefficient v of a fluid of interest with respect to each of the varying flow velocity V, and, from among values of δs calculated from Equation (4) with respect to each of the varying flow velocity V, the value which provides a highest coefficient of correlation between FIR (%) and the prominent peak projected area A in Equation (1) is selected as δs in Equation (6), $$\delta s = \frac{y^+ \times v}{u^*} \quad (4)$$

$$u^* \sqrt{\frac{\tau_0}{\rho}}. \quad (5)$$

5. The method according to claim 4, wherein the prominent peak projected area A is calculated in such a manner that highest roughness Rz, ten point average roughness Rzjis, root mean square roughness Rq or average height of roughness curve element Rc is measured as roughness height R", the slope a of the arithmetic average roughness Ra to the measured parameter R" is determined, and the parameter R" is converted assuming that Ra=a×R" where R" is is Rz, Rzjis, Rq or Rc.

6. A surface performance estimating apparatus for estimating surface performance by the prediction method described in claim 1, the apparatus comprising:
a measurement section configured to measure a roughness height R and an average length RSm of roughness curve elements; and
a calculation unit configured to calculate the prominent peak projected area A and to calculate the friction increase ratio FIR (%) using Equation (1) or the frictional resistance increase Δτ using Equation (2).

7. The surface performance estimating apparatus according to claim 6, wherein the measurement section is configured to measure the roughness height R and the average length RSm of roughness curve elements of three dimensional roughness while reading a travel distance with a rotary encoder or a linear encoder and reading a displacement with a laser displacement meter using a two-dimensional beam.

8. The surface performance estimating apparatus according to claim 6, wherein the roughness height R measured is highest roughness Rz, ten point average roughness Rzjis, root mean square roughness Rq, average height of roughness curve elements Rc or arithmetic average roughness Ra.

9. The method according to claim 1, wherein the surface roughness meter is a stylus profilometer or a laser displacement meter.

10. The method according to claim 1, wherein in the measuring, roughness height R and average length RSm of roughness curve elements of three dimensional roughness of the rough surface are measured.

11. The method according to claim 10, wherein the roughness height R measured is highest roughness Rz, ten point average roughness Rzjis, root mean square roughness Rq, average height of roughness curve elements Rc or arithmetic average roughness Ra.

12. The method according to claim 1, wherein the frictional resistant test to predetermine the coefficient C or the coefficient Cr is a towing test, a circular tube test, a double cylinder test, or a cavitation tank test.

13. The method according to claim 1, wherein the frictional resistant test to predetermine the coefficient C or the coefficient Cr is a double cylinder test using a double circular cylinder device.

14. A surface performance estimating apparatus for estimating surface performance, comprising:
a measurement section configured to measure a roughness height R and an average length RSm of roughness curve elements; and
a calculation unit configured to calculate a prominent peak projected area A, which is a total projected area of all prominent peaks standing out above a viscous sublayer thickness per unit area, and to calculate a friction increase ratio FIR (%) using Equation (1) or a frictional resistance increase ΔT using Equation (2):

$$FIR(\%) = C \times A \quad (1)$$

$$\Delta \tau = C_r \frac{1}{2} \rho A V^2, \quad (2)$$

wherein in Equation (1), the coefficient C is a constant dependent on the prominent peak projected area A and is predetermined by performing a frictional resistance test beforehand in which frictional resistances are measured with respect to a plurality of rough surfaces having different degree of roughness while changing a flow velocity V and friction increase ratios FIR (%) of the plurality of rough surfaces are calculated, wherein the friction increase ratios FIR (%) are percentages of differences $\tau_r - \tau_0$ between frictional resistances $\tau_r$ of the plurality of rough surfaces and a frictional resistance $\tau_0$ of a smooth surface, divided by $\tau_0$, and
in Equation (2), the coefficient $C_r$ is a constant dependent on a fluid density ρ, the prominent peak projected area A and the flow velocity V, and is predetermined from the relation of Equation (2) using values of frictional resistance increase Δτ obtained beforehand by a frictional resistance test in which frictional resistances are measured with respect to a plurality of rough surfaces having different degree of roughness while changing a flow velocity V, wherein the values of frictional resistance increase Δτ are differences $\tau_r - \tau_0$ between frictional resistances $\tau_r$ of the plurality of rough surfaces and a frictional resistance $\tau_0$ of a smooth surface.

15. The surface performance estimating apparatus according to claim 14, wherein the measurement section is configured to measure the roughness height R and the average length RSm of roughness curve elements of three dimensional roughness while reading a travel distance with a rotary encoder or a linear encoder and reading a displacement with a laser displacement meter using a two-dimensional beam.

16. The surface performance estimating apparatus according to claim 14, wherein the roughness height R measured is highest roughness Rz, ten point average roughness Rzjis, root mean square roughness Rq, average height of roughness curve elements Rc or arithmetic average roughness Ra.

* * * * *